United States Patent
Ju et al.

(10) Patent No.: US 11,388,892 B2
(45) Date of Patent: Jul. 19, 2022

(54) METHOD FOR PREPARING CKO/KI ANIMAL MODEL BY USING CAS9 TECHNOLOGY

(71) Applicant: GEMPHARMATECH CO., LTD, Jiangsu (CN)

(72) Inventors: Cunxiang Ju, Jiangsu (CN); Jing Zhao, Jiangsu (CN); Mingkun Zhang, Jiangsu (CN); Song Li, Jiangsu (CN); Huanhuan Hou, Jiangsu (CN)

(73) Assignee: GEMPHARMATECH CO., LTD, Jiangsu (CN)

( * ) Notice: Subject to any disclaimer, the term of this patent is extended or adjusted under 35 U.S.C. 154(b) by 0 days.

(21) Appl. No.: 17/280,178

(22) PCT Filed: Feb. 22, 2019

(86) PCT No.: PCT/CN2019/075880
§ 371 (c)(1),
(2) Date: Mar. 25, 2021

(87) PCT Pub. No.: WO2020/077930
PCT Pub. Date: Apr. 23, 2020

(65) Prior Publication Data
US 2021/0307303 A1 Oct. 7, 2021

(30) Foreign Application Priority Data
Oct. 17, 2018 (CN) .......................... 201811208538.6

(51) Int. Cl.
*A01K 67/027* (2006.01)
*C12N 9/22* (2006.01)
*C12N 15/11* (2006.01)
*C12N 15/90* (2006.01)

(52) U.S. Cl.
CPC ...... *A01K 67/0276* (2013.01); *A01K 67/0278* (2013.01); *C12N 9/22* (2013.01); *C12N 15/11* (2013.01); *C12N 15/907* (2013.01); *A01K 2217/072* (2013.01); *A01K 2217/075* (2013.01); *A01K 2227/105* (2013.01); *A01K 2267/03* (2013.01); *C12N 2310/20* (2017.05); *C12N 2800/80* (2013.01)

(58) Field of Classification Search
None
See application file for complete search history.

(56) References Cited

U.S. PATENT DOCUMENTS
11,021,719 B2 * 6/2021 Gong .................. C12N 9/2471

FOREIGN PATENT DOCUMENTS

| CN | 107043787 A | 8/2017 |
|---|---|---|
| CN | 108424930 A | 8/2018 |
| CN | 108504657 A | 9/2018 |
| CN | 109266680 A | 1/2019 |
| WO | 2018069474 A1 | 4/2018 |
| WO | 2018177440 A1 | 10/2018 |

OTHER PUBLICATIONS

Sakurai et al. A single blastocyst assay optimized for detecting CRISPR/Cas9 system-induced indel mutations in mice (BMC Biotech, 2014, 14:1-11) (Year: 2014).*
Fujii et al., Efficient generation of large-scale genome-modified mice using gRNA and CAS9 endonuclease (NAR, 2013, 41:1-9) (Year: 2013).*
Kouranova et al., CRISPRs for Optimal Targeting: Delivery of CRISPR Components as DNA, RNA, and Protein into Cultured Cells and Single-Cell Embryos (Hum Gen Ther, 2016, 27:464-475) (Year: 2016).*
Hwang et al., Efficient genome editing in zebrafish using a CRISPR-Cas system (Nat Biotech, 2013, 31:227-229) (Year: 2013).*
Raveux et al., Optimization of the production of knock-in alleles by CRISPR/Cas9 microinjection into the mouse zygote. Sci Rep. Feb. 17, 2017;7:42661 (Year: 2017).*
Li, Zhongyi et al.; Rat Models of AR and IRS2 Knockout Genes Were Prepared Using CRISPR/Cas9 Technology; Journal of Tropical Medicine, vol. 18, No. 9, Sep. 28, 2018, ISSN: 1672-3619, pp. 1143-1146.
Kelli J. C. et al.; A mouse model for adult cardiac-specific gene deletion with CRISPR/Cas9; Proceedings of The National Academy of Sciences of The United States of America, vol. 113, No. 2, Jan. 12, 2016, ISSN: 0027-8424, pp. 338-343.
Li, Lihong et al.; Application of Next Generation Gene Editing Techniques in Animal Model of Human Disease; Experimental Animal Science; vol. 34, No. 3, pp. 76-80, Jun. 30, 2017.
Wu, Xi et al.; Designation and Activity Verification of High Efficiency sgRNAs for Hipp11 Locus; Experimental Animal Science; vol. 32, No. 5, pp. 26-30, Oct. 31, 2015.
Shen, Yangkun et al.; The Application of CRISPR/Cas9 System in Disease Models and Gene Therapy; Chinese Journal of Biochemistry and Molecular Biology; vol. 31, No. 8, pp. 786-794, Aug. 31, 2015.

* cited by examiner

*Primary Examiner* — Arthur S Leonard
(74) *Attorney, Agent, or Firm* — Novick, Kim & Lee, PLLC; Allen Xue

(57) ABSTRACT

A method for preparing a CKO/KI animal model by using Cas9 technology includes a Cas9 protein expressed and purified in vitro, high-efficiency sgRNA(s) screened by sgRNA cleavage efficiency test on embryos in advance, and single-stranded DNA as targeting vector(s) are mixed with Cas9 protein and sgRNA(s) and then subjected to embryo injection and transplantation; mice born after transplantation are marked as F0 and the genotype identification of F0 is carried out; sexually mature F0 with the correct genotype are bred, and the offspring mice thereof are marked as F1; and the F1 mice are analyzed and verified, and the F1 mice with the correct genotype are the prepared CKO/KI animal model.

1 Claim, 9 Drawing Sheets

Specification includes a Sequence Listing.

A

B

A

B

A

B

SEQUENCE LISTING

<160> NUMBER OF SEQ ID NOS: 65

<210> SEQ ID NO 1
<211> LENGTH: 23
<212> TYPE: DNA
<213> ORGANISM: Artificial Sequence
<220> FEATURE:
<223> OTHER INFORMATION: synthesized

<400> SEQUENCE: 1
tggctcacaa acatccgtaa tga                                           23

<210> SEQ ID NO 2
<211> LENGTH: 23
<212> TYPE: DNA
<213> ORGANISM: Artificial Sequence
<220> FEATURE:
<223> OTHER INFORMATION: synthesized

<400> SEQUENCE: 2
cagtcagtaa acggatcaaa gct                                           23

<210> SEQ ID NO 3
<211> LENGTH: 20
<212> TYPE: DNA
<213> ORGANISM: Artificial Sequence
<220> FEATURE:
<223> OTHER INFORMATION: synthesized

<400> SEQUENCE: 3
gaacactagt gcacttatcc                                               20

<210> SEQ ID NO 4
<211> LENGTH: 20
<212> TYPE: DNA
<213> ORGANISM: Artificial Sequence
<220> FEATURE:
<223> OTHER INFORMATION: synthesized

<400> SEQUENCE: 4
ctgagccaac agtggtagta                                               20

<210> SEQ ID NO 5
<211> LENGTH: 20
<212> TYPE: DNA
<213> ORGANISM: Artificial Sequence
<220> FEATURE:
<223> OTHER INFORMATION: synthesized

<400> SEQUENCE: 5
aacactagtg cacttatcct                                               20

<210> SEQ ID NO 6

```
<211> LENGTH: 20
<212> TYPE: DNA
<213> ORGANISM: Artificial Sequence
<220> FEATURE:
<223> OTHER INFORMATION: synthesized

<400> SEQUENCE: 6
ccaacagtgg tagtaaggta                                                   20

<210> SEQ ID NO 7
<211> LENGTH: 18
<212> TYPE: DNA
<213> ORGANISM: Artificial Sequence
<220> FEATURE:
<223> OTHER INFORMATION: synthesized

<400> SEQUENCE: 7
tggtagtaag gtaagggc                                                     18

<210> SEQ ID NO 8
<211> LENGTH: 21
<212> TYPE: DNA
<213> ORGANISM: Artificial Sequence
<220> FEATURE:
<223> OTHER INFORMATION: synthesized

<400> SEQUENCE: 8
ccaacagtgg tagtaaggta a                                                 21

<210> SEQ ID NO 9
<211> LENGTH: 20
<212> TYPE: DNA
<213> ORGANISM: Artificial Sequence
<220> FEATURE:
<223> OTHER INFORMATION: synthesized

<400> SEQUENCE: 9
tctggaaaaa gcagtcccac                                                   20

<210> SEQ ID NO 10
<211> LENGTH: 685
<212> TYPE: DNA
<213> ORGANISM: Artificial Sequence
<220> FEATURE:
<223> OTHER INFORMATION: synthesized

<400> SEQUENCE: 10
tggctcacaa acatccgtaa tgagatgccc tctacgggtg catctgaaga cagctacagt        60
gtacttagat ataataataa taataaataa atccttttaa aaaaaaagct tgttgaatcc       120
aacaaagcag ccatgaggac tccacttgct cacttaacct tgccaccttg tcaatttgcc       180
atctgagctt tctttgtcat ggtatttata tgttgttctt cctggctgct ggactgtgct       240
gacggtcacc ctgcaaacat gtgcagtcct aaaatgccag tcattgtgat gccaggagga       300
cagacagaat atttattttg atatcctcga aaatgtcaca atgctgagag aactggtcat       360
ttgttgtcag acacaaatgc ctgtgacaat tcttgcaggt actttctgca gaaaatacaa       420
tccagtctgc aagagctgcc ctccaagtac cttctccagc ataggtggac agccgaactg       480
taacatctgc agagtgtgtg caggtaggtc agtctgtctg tctgtctgtc tgtctggaaa       540
ggagagcttg ctgttgccca ggctagactg gaacctgtga ctcttgttcc tcagcctccc       600
aagtctggag gtttgcttta gaggggagac atcttcatct ttaagaccat gggcagagt        660 taagctttga tccgtttact gactg                                             685
```

<210> SEQ ID NO 11
<211> LENGTH: 6613
<212> TYPE: DNA
<213> ORGANISM: Artificial Sequence
<220> FEATURE:
<223> OTHER INFORMATION: synthesized

<400> SEQUENCE: 11

| | | | | | |
|---|---|---|---|---|---|
| tgacagaagg | ctgttaaatc | gaatgaacct | acatggttca | aatacaaggg | atacaagatt | 60 |
| gtcagtcctg | gaagtctttc | ttttataaaa | tatgtgaatg | aagtgttggt | gtcttctaga | 120 |
| ggtgacacct | aagggttctg | aaaaaataaa | atgtatagac | ccttatgtac | agacctgtgt | 180 |
| ataaactttt | gtacatacaa | atagggtagc | ttttttttgaa | cttatacata | cagctgtaca | 240 |
| taaagtaact | atcagttagg | cttgtgtcaa | ctgtttggat | ttttttcact | tgaatatttg | 300 |
| ggactttttc | ttttggttta | ttaaaagtta | catatgccac | gtgtgtgaac | gatatggctg | 360 |
| gtactgtgtt | tatttcttcc | atgaactaag | acagtctaaa | tgagttcctt | tcacgtttta | 420 |
| attttacctt | aggacttctg | gaatttcttc | tgcacataaa | gttctgatag | cattagttta | 480 |
| agctggacta | accctgaaag | tagcttgtgg | caagtatcaa | ggaatcaata | ttatactcta | 540 |
| caaaatcaaa | gtttacagag | aagtcatata | gtaattttc | tgaaatttac | tggcacaatg | 600 |
| ttaatccagc | ctgactccaa | ctaattaatg | gtcacattaa | tttaagtctt | tcccttgcct | 660 |
| ctgctgcatt | agtttctctc | aaaattgtta | acttacaact | tgaagtctgg | tattataaat | 720 |
| tgaatgtaaa | gcattctgaa | agatactata | ctgattgcag | gttttcagt | caggttcaag | 780 |
| ctaatttgac | cagtcattgg | attaattatg | gatctggggc | cataaatgct | atttaattc | 840 |
| cactatagag | attaaaataa | gccattctcc | atttcataat | attctattgg | actttgactg | 900 |
| caggggcctc | caagtcttga | cagtagatta | taatccttca | gctgcccact | ctactggagg | 960 |
| aggacaaact | ggtcactttt | cagcaaaacc | tggctgtgga | tcagggcagt | ctggtacttc | 1020 |
| caagctcatt | agatgccatc | atgctctcac | tgcctcctca | gcttcaagag | gaatctggaa | 1080 |
| aaagcagtcc | cactggtcag | gaaaggaaca | ctagtgcact | tatcctgggt | gtctgctgag | 1140 |
| ctcgagagtc | gaccttaatt | aaggccgtct | cctacgcctc | ccgctcttca | ctagagctgg | 1200 |
| ccatcactat | ccttctcttt | actgcttct | tctcttttgc | tactgacttt | tgtctctgtt | 1260 |
| aaacaccacc | gggaagtaca | gagggctcag | tgagtacagg | ggcctgcagc | caaacctggc | 1320 |
| aacccgagtt | aaggcctgga | acccacatgg | tgggaggagt | gcccatcctg | caacttgtcc | 1380 |
| tctggcctcc | acatgcacat | tgtaacacaa | atccaaaaca | taaatttaaa | tgtaataaaa | 1440 |
| agttaaaata | ccacctacca | ctgtttgtta | actggtctcc | ctgggttggc | tctgaactca | 1500 |
| ctatgtcacg | atgaaccttg | aactcttttc | tttttctagt | taattgcttt | gtgtgatttt | 1560 |
| ttaaaaagat | ttattcattt | attatatata | agtgcactgc | agctgtcttc | agacacacca | 1620 |
| gaagagggca | tcagatccca | ttacagggcg | cgcccatgag | gattccaaca | ccaagccatt | 1680 |
| ctataaataa | gaagccgagt | ctcagagaat | ttgagtgtgt | agagaaagga | ggtccgcagg | 1740 |
| cccagttctg | tgcatcatag | ggtgttccgg | ggtgtctggc | tgtatctcaa | gattctctca | 1800 |
| gaaaatcacc | cgcaccggac | cggatccctc | agggaggggc | tgcactttgg | ttcttctctt | 1860 |
| ctgcacccgg | atgaagcagg | aaccccggtt | gcgtgttgca | ctgaacgcta | aagggttaag | 1920 |
| gcctgggggg | ccgcccttt | tccgcccagc | cggcggagt | atgaataccc | tcgctccagc | 1980 |
| tccctgctgg | agttctccgc | ttccgctggg | tcactgtcgc | cgctacttct | tttcaacccc | 2040 |

-continued

```
taaaagctcc acgggccact cccttctcta gtgctccacg tccgcttgcc ctcggggggcc    2100
agaccagcga cgccgccacc atggtgccca agaagaagag gaaagtctcc aacctgctga    2160
ctgtgcacca aaacctgcct gccctccctg tggatgccac ctctgatgaa gtcaggaaga    2220
acctgatgga catgttcagg gacaggcagg ccttctctga acacacctgg aagatgctcc    2280
tgtctgtgtg cagatcctgg gctgcctggt gcaagctgaa caacaggaaa tggttccctg    2340
ctgaacctga ggatgtgagg gactacctcc tgtacctgca agccagaggc ctggctgtga    2400
agaccatcca acagcacctg gccagctca acatgctgca caggagatct ggcctgcctc    2460
gcccttctga ctccaatgct gtgtccctgg tgatgaggag aatcagaaag gagaatgtgg    2520
atgctgggga gagagccaag caggccctgg cctttgaacg cactgacttt gaccaagtca    2580
gatccctgat ggagaactct gacagatgcc aggacatcag gaacctggcc ttcctgggca    2640
ttgcctacaa caccctgctg cgcattgccg aaattgccag aatcagagtg aaggacatct    2700
cccgcaccga tggtgggaga atgctgatcc acattggcag gaccaagacc ctggtgtcca    2760
cagctggtgt ggagaaggcc ctgtccctgg gggttaccaa gctggtggag agatggatct    2820
ctgtgtctgg tgtggctgat gaccccaaca actacctgtt ctgccgggtc agaaagaatg    2880
gtgtggctgc cccttctgcc acctcccaac tgtccacccg ggccctggaa gggatctttg    2940
aggccaccca ccgcctgatc tatggtgcca aggatgactc tgggcagaga tacctggcct    3000
ggtctgggca ctctgccaga gtgggtgctg ccagggacat ggccagggct ggtgtgtcca    3060
tccctgaaat catgcaggct ggtggctgga ccaatgtgaa cattgtgatg aactacatca    3120
gaaacctgga ctctgagact ggggccatgg tgaggctgct cgaggatggg gactgaactc    3180
ctcaggtgca ggctgcctat cagaaggtgg tggctggtgt ggccaatgcc ctggctcaca    3240
aataccactg agatctttt ccctctgcca aaaattatgg ggacatcatg aagcccttg    3300
agcatctgac ttctggctaa taaaggaaat ttattttcat tgcaatagtg tgttggaatt    3360
ttttgtgtct ctcactcgga aggacatatg ggagggcaaa tcatttaaaa catcagaatg    3420
agtatttggt ttagagtttg gcaacatatg cccatatgct ggctgccatg aacaaaggtt    3480
ggctataaag aggtcatcag tatatgaaac agcccctgc tgtccattcc ttattccata    3540
gaaaagcctt gacttgaggt tagatttttt ttatattttg ttttgtgtta ttttttttcttt    3600
taacatccct aaaattttcc ttacatgttt tactagccag atttttcctc ctctcctgac    3660
tactcccagt catagctgtc cctcttctct tatggagatc cctcgacctg cagggaaggt    3720
gggcagcaac tggcacacct caagatgtcc cttagtctgg aggtggctac atacaggtac    3780
acagtgctga ctgtcctcgg cttcttctgc ggcccagaaa cttggctttg tactttctgt    3840
gactgtcagc tatcgctttg taaaactgtc ctatttatgt gtatttgtgt atgtaccaca    3900
tgtgtacagg tgtcctaaga gcccagagga aggcaatggg ttgtgtgcag ctccacactg    3960
gtgctgtgaa ccaaacccct gttctcagca aaaagcagca agcattctta accactgagc    4020
cgtctgtcca gccctcggag tcacttaaaa cgttttataa catttactta tgtaatgtat    4080
ttgtctggga tggaggctta tgagtcccag aggtggaaca ggtctggctt ggcagcttgg    4140
cccacccagt tcaggacca gaagagacgt gatgcttaa aaagacagct cagtcttcag    4200
ggaggagacc agacagatga gttctttgga aggcaggcaa tctccagtgt ctatgccaac    4260
atcctgggga cacctgggca gtctcagaag agaggccttg caggtttgcc tgatcatgct    4320
aacctgccac ctcgcctggg cctcaggtgt tttgggtaag agctggcctc ctagcttttt    4380
tgcttccttt caagccctca tgtcactggt cctgcccag ttctctgccc ttttcttggc    4440
```

```
tgcctcagga cggctgagtg gaacggctct ggtggtatgt tcacagcctc tgtctgtgtc    4500
tcttgtggga aaaggcccca gttggagtcc cacggttgag ggctgaggat atcactccag    4560 agtatgggc taggacagga tgccccctt ttccagaatc cagcggtaaa gaggaaagac      4620
agagacaggt ctaggagagg agctggaggg cccagagaag acagccagt gagtgtctag     4680 gaaagactga atgcataagg caggatgccg catgaggaca gaggaaaggc tactttgaga    4740
accagatgtg ctcagaggcc atgaatggaa acagactagt tccgaatccc atgtgaactg    4800
atttccctca tctccttcaa tcagctccat aggccactga ggcagggcca tgaacgttaa    4860
gacctctgcc ctgaagagtt tgtgatcctg agatgagggc tttagcccca gtcagtcctc    4920 tgagggaag ggtccaggca gctctgagga atgtaaccac tggcgtttga ggtctgaaaa     4980
ggatttggag aaggggagct gaattcattt gcttttgtct gttaccagct ctgggggcag    5040
agagagagcc atcccctggg aacagcctga gaattcccac ttcccctgag gagccctccc    5100
ttcttaggcc ctccagatgg tagtgtggac aaaaggcaat aattagcatg agaatcggcc    5160
tccctcccag aggatgaggt catcggcctt ggccttgggt ggggaggcgg agactgatct    5220
gaggagtctg atataagtgt tagcaattca tttggccctg cctccgactg tgggaatctg    5280
catgtggggt ctccctgtgt ctcaaatatg ggttggctaa gtatatatct gtgggtatat    5340
gactgtgtgg cttttatatg acaatggtca caatagagat tgatcctgca gtggcaggac    5400
atgctacctc agctggagct gaccctatct ccccctccc caccaggact ctgctggagg     5460
ctgagaactc tcggttgcag acacctgac gaggttccca ggcttctctt ggctttctgg     5520
gtaagaggcg gagccaactg ctctccttgg aagatcgtaa gggcaggatg tgtcaaactg    5580
ccaatagaga actacttact cttcaggctg aagctgatgg aacaggtaac aaaggcaaac    5640
actaatcatg atcagcaaga tgaagcagaa agggaacaag gggatattaa atgtgtatag    5700
acacgctaga gagatggctc agcagttaag agaactagct ggtctttcag aggtcctgag    5760
atcaatttta gacacccaca tggtggctca tgaccatcta tctataaatg gatctgattt    5820
tcatgtctgg cagtgtacag aagctaactg aagaaaggtg gaagacccac aagagttcaa    5880
gataagccct atatagtgaa gttcaaggca agctttttct acctgaaact tagtctcaaa    5940
aaaaaatgaa tacgtaaaca gtcttccagg ggataagaac cttacagaaa agcagaaat    6000 gcctgggca ctggattacc gatgtaatca aattcagtcc ttgaattgaa cacaggattg     6060
cctagagcaa ggccagccag agattcatct cagagggaga aggtgtctt tggagcaatt     6120 ttgtggtaat ctagtatgta tcacataagt ttagacgcat ttgggactgg aaagatgtga    6180
acaaagcacc ctatggctca catctgtcat taactctagt tccagtgcac ctgacaccgt    6240
cttctggcct ctgcagtgac caagcacatg ggtagtatgt agacatatac ataagcaaaa    6300
cacacatcat taaaaagtga catttcccaa aggaagctga agaaccagtt cttgagaaga    6360
tagtagaaat cagaagggga aatagtagac atacagaggg actgaccagg ttgtgtcacc    6420
tttataggct aggctaatgg atgatcgaca ctagcgctct ttgtgaagga cacacaaatg    6480
agacatagtt tataggacta aacacacttc taagcaattt aatgagactt aagaccctgt    6540
ctctagcaaa tactctggat gatattcagc tcaaggctct tgtcagacat gtttccattt    6600
tcaaggtgag cta                                                       6613
```

<210> SEQ ID NO 12
<211> LENGTH: 29
<212> TYPE: DNA

```
<213> ORGANISM: Artificial Sequence
<220> FEATURE:
<223> OTHER INFORMATION: synthesized

<400> SEQUENCE: 12
ggcacaatgt taatccagcc tgactccaa                                      29

<210> SEQ ID NO 13
<211> LENGTH: 31
<212> TYPE: DNA
<213> ORGANISM: Artificial Sequence
<220> FEATURE:
<223> OTHER INFORMATION: synthesized

<400> SEQUENCE: 13
gcttgccttg aacttcacta tatagggctt a                                   31

<210> SEQ ID NO 14
<211> LENGTH: 29
<212> TYPE: DNA
<213> ORGANISM: Artificial Sequence
<220> FEATURE:
<223> OTHER INFORMATION: synthesized

<400> SEQUENCE: 14
ggggccataa atgctatttt aattccact                                      29

<210> SEQ ID NO 15
<211> LENGTH: 29
<212> TYPE: DNA
<213> ORGANISM: Artificial Sequence
<220> FEATURE:
<223> OTHER INFORMATION: synthesized

<400> SEQUENCE: 15
ccacctttct tcagttagct tctgtacac                                      29

<210> SEQ ID NO 16
<211> LENGTH: 25
<212> TYPE: DNA
<213> ORGANISM: Artificial Sequence
<220> FEATURE:
<223> OTHER INFORMATION: synthesized

<400> SEQUENCE: 16
atgcccacca aagtcatcag tgtag                                          25

<210> SEQ ID NO 17
<211> LENGTH: 21
<212> TYPE: DNA
<213> ORGANISM: Artificial Sequence
<220> FEATURE:
<223> OTHER INFORMATION: synthesized

<400> SEQUENCE: 17
ccttaactcg ggttgccagg t                                              21

<210> SEQ ID NO 18
<211> LENGTH: 25
<212> TYPE: DNA
<213> ORGANISM: Artificial Sequence
<220> FEATURE:
<223> OTHER INFORMATION: synthesized

<400> SEQUENCE: 18
cctcctctcc tgactactcc cagtc                                          25
```

<210> SEQ ID NO 19
<211> LENGTH: 23
<212> TYPE: DNA
<213> ORGANISM: Artificial Sequence
<220> FEATURE:
<223> OTHER INFORMATION: synthesized

<400> SEQUENCE: 19
tcacagaaac catatggcgc tcc                                           23

<210> SEQ ID NO 20
<211> LENGTH: 20
<212> TYPE: DNA
<213> ORGANISM: Artificial Sequence
<220> FEATURE:
<223> OTHER INFORMATION: synthesized

<400> SEQUENCE: 20
agtcttctgg gcaggcttaa                                               20

<210> SEQ ID NO 21
<211> LENGTH: 23
<212> TYPE: DNA
<213> ORGANISM: Artificial Sequence
<220> FEATURE:
<223> OTHER INFORMATION: synthesized

<400> SEQUENCE: 21
agacagccgg gtacgagtcg tga                                           23

<210> SEQ ID NO 22
<211> LENGTH: 28
<212> TYPE: DNA
<213> ORGANISM: Artificial Sequence
<220> FEATURE:
<223> OTHER INFORMATION: synthesized

<400> SEQUENCE: 22
cagcctggca atatgtaaga tacatcag                                      28

<210> SEQ ID NO 23
<211> LENGTH: 22
<212> TYPE: DNA
<213> ORGANISM: Artificial Sequence
<220> FEATURE:
<223> OTHER INFORMATION: synthesized

<400> SEQUENCE: 23
gtgcaagcac gtttccgact tg                                            22

<210> SEQ ID NO 24
<211> LENGTH: 27
<212> TYPE: DNA
<213> ORGANISM: Artificial Sequence
<220> FEATURE:
<223> OTHER INFORMATION: synthesized

<400> SEQUENCE: 24
ctggtttcat gagtcatcag acttcta                                       27

<210> SEQ ID NO 25
<211> LENGTH: 20
<212> TYPE: DNA
<213> ORGANISM: Artificial Sequence
<220> FEATURE:

<223> OTHER INFORMATION: synthesized

<400> SEQUENCE: 25
tcaagggatg ctcttcaata                                         20

<210> SEQ ID NO 26
<211> LENGTH: 20
<212> TYPE: DNA
<213> ORGANISM: Artificial Sequence
<220> FEATURE:
<223> OTHER INFORMATION: synthesized

<400> SEQUENCE: 26
gagaggccca atgcccaacg                                         20

<210> SEQ ID NO 27
<211> LENGTH: 1591
<212> TYPE: DNA
<213> ORGANISM: Artificial Sequence
<220> FEATURE:
<223> OTHER INFORMATION: synthesized

<400> SEQUENCE: 27

| | | | | |
|---|---|---|---|---|
| ttctagttca aggccagtct | gacctacaca gtgggttctg | tcatggcctg gatcatatat | 60 |
| ataatcagac cttggtttca | aaacctcctg accatggtca | cgaatgaaca atttaatatg | 120 |
| cattaccaga attctgaaaa | ataaactgta atttggacta | tgagatttag acgacaaaat | 180 |
| tatagaatac ttagaatttc | tgatgaaaaa gaaatcgtgt | aaatgtgcag tgtgtaggat | 240 |
| aaactaaaaa actgtttatc | tgaaattcac atttaattgg | gtgtctcgta attaatccag | 300 |
| caaccctaac tgaaatgtaa | caggtaatat atcttgttgc | atatagactt tatttaatga | 360 |
| aatagttgtt tcaatatttt | atgtttgtga acattctgaa | tgacagtatt caaaagcatt | 420 |
| tgaaagccac tgctgtccta | ggtaatgaag ttttacaaaa | ctttattgag acaggatctc | 480 |
| actttgtgat ctagacaaac | ttcaaacttc attgcaatcc | tcctgcctca gcttcccaga | 540 |
| tctggggatt ataggctgag | ccactatgcc tggtttattc | ttaataatgt ggagaagtct | 600 |
| agaactttct tatttgtgca | cagtaaaggt cttcagttaa | catgattgtg aatcacactg | 660 |
| atgctgtgat tgtagtgtta | tttgtaatgt actgttcatt | attttttatgt actcaacaat | 720 |
| ctgttatctt ttatgactag | ttctgacaga atatgaaaaa | tgtaggttag tcatagtagg | 780 |
| gtctcagtct ggaggcctgt | aaaagagaga tgctgactgt | aacagtgcaa agaacctaac | 840 |
| atgtacctaa ctgagaccta | acaattacac attttcaag | ggatgctctt caatatgaca | 900 |
| taacttcgta tagcatacat | tatacgaagt tatgatatcc | atatgtgtct tttggggata | 960 |
| agcttgattg aaagacaagc | tcccgagctt acactatgca | gcagccactt acccttttgac | 1020 |
| agcttcagct gagaacatag | tcgtatatat ttaatatgga | cagtgtttat tggattaaaa | 1080 |
| agtagtccat agaatacccca | aagaaatgtg aagataatc | agatcccttt ttcacttttt | 1140 |
| tccctagcaa cttttttaatt | gtcagtctct acataaacta | agtttgccag acaatgattt | 1200 |
| aacaacatta ccagcctcca | ttgcaaatct tattaatctc | agggaactgg atgtcagcaa | 1260 |
| aaatggtaag tcctcgaaat | tcttgtcctt ggagatacat | ttcattggta ggatttctgt | 1320 |
| tttccaaatg tttaatagtc | agattgcaat atattagtgt | catagaatct attctacata | 1380 |
| aatatgaaaa catttttccca | tttcaaaagt tttataatac | aataaaattg agcatcatat | 1440 |
| cctcagctta gaatttattt | ataaatataa agtttatgat | acctcaaaac acctggggga | 1500 |
| aaaaagtaga ttttaaatat | attattacag tccacgttgg | gcattgggcc tctcagattt | 1560 |

-continued ctctctccca actgaaagtt tgtacctgaa t    1591

<210> SEQ ID NO 28
<211> LENGTH: 23
<212> TYPE: DNA
<213> ORGANISM: Artificial Sequence
<220> FEATURE:
<223> OTHER INFORMATION: synthesized

<400> SEQUENCE: 28
ggaaccatta gatttaacca gac    23

<210> SEQ ID NO 29
<211> LENGTH: 23
<212> TYPE: DNA
<213> ORGANISM: Artificial Sequence
<220> FEATURE:
<223> OTHER INFORMATION: synthesized

<400> SEQUENCE: 29
ctgtttacaa agtctaaggt gtg    23

<210> SEQ ID NO 30
<211> LENGTH: 23
<212> TYPE: DNA
<213> ORGANISM: Artificial Sequence
<220> FEATURE:
<223> OTHER INFORMATION: synthesized

<400> SEQUENCE: 30
ttgtttatta cagtctgtat ccc    23

<210> SEQ ID NO 31
<211> LENGTH: 25
<212> TYPE: DNA
<213> ORGANISM: Artificial Sequence
<220> FEATURE:
<223> OTHER INFORMATION: synthesized

<400> SEQUENCE: 31
agatgttgga gctcgatatc ataac    25

<210> SEQ ID NO 32
<211> LENGTH: 23
<212> TYPE: DNA
<213> ORGANISM: Artificial Sequence
<220> FEATURE:
<223> OTHER INFORMATION: synthesized

<400> SEQUENCE: 32
gatgctcttc aatatgacat aac    23

<210> SEQ ID NO 33
<211> LENGTH: 23
<212> TYPE: DNA
<213> ORGANISM: Artificial Sequence
<220> FEATURE:
<223> OTHER INFORMATION: synthesized

<400> SEQUENCE: 33
tctgagaggc ccaatgccca acg    23

<210> SEQ ID NO 34
<211> LENGTH: 20
<212> TYPE: DNA

```
<213> ORGANISM: Artificial Sequence
<220> FEATURE:
<223> OTHER INFORMATION: synthesized

<400> SEQUENCE: 34
gagctaccct gagtagcaga                                                    20

<210> SEQ ID NO 35
<211> LENGTH: 20
<212> TYPE: DNA
<213> ORGANISM: Artificial Sequence
<220> FEATURE:
<223> OTHER INFORMATION: synthesized

<400> SEQUENCE: 35
ctggtcatca gccagctaag                                                    20

<210> SEQ ID NO 36
<211> LENGTH: 3758
<212> TYPE: DNA
<213> ORGANISM: Artificial Sequence
<220> FEATURE:
<223> OTHER INFORMATION: synthesized

<400> SEQUENCE: 36
tgacccagtc ttcaccaact ctgcatggaa tctagggatc ctggcccttg aggagcgcca        60
gacccagctc ataggccacg cccaccctca ggtctaagtg acattagatt atctgtatgt       120
tcatcatcca tggtacagct gagaacatca aggagggaaa gtggcagtcc tacttttcgc       180
catgtggtga tggagaccat ttctgggcaa ggctacatgg tgcggatgga tgtctctggg       240
tttgcctctg ctgaagtctg cttgctcact gcagacagct ctgccacgta tctctggctt       300
cctttctgcg ctggaagatt tcacatacct tgtttgccag gtgttttggg cctcagttct       360
cccccatcc agcttctccc taactggccc ctcttctttg cctctgaccc ctgctttctg        420
agcccataac cttagctgtg gcagcacagc ctctctcttt gtaccctgg gagggaacca        480
tgcccggtta gtattgtcaa atacccccaca tcagaggcgg gtgtgaggtt tggggtgcag       540
tgccctgggc catgtaatcg ggtagaattc cctccctata tgactactca atccgtggga       600
ggagagggca gagggctgga aaggatgcag ctggggacat gtctattcgc actggcgctt       660
tctctacgag cccagttgc caaatgacta catcggctaa agagagctgg cagcccagac        720
agagttgagg ccagagcagc ttcaaagatg tcttggtgcc tgtttcctgt gtgcatgtca       780
gtctcctctg ggtaaggccc acatgtgtgt gctcagcaag tctgtatttc cttgaccctg       840
agccttctga ccgtacctac atacccaacc gcacctatat acccgaccgc aggttcaact       900
gctgacatca tatgggtccc agtagtgggt acttttgagt gctggtggaa tgttatgtgt       960
tatgtgtcag tgtgcattta tgtggcaaga agcttgccag tgcggcaggc atttcctgag      1020
aagagccatg agaccctgca tgctgcctga ccctggcagt accacccagg cttctgaggc      1080
ggaaagaacc agctggtcta gaaatattca attccgatca tattcaataa cccttaatag      1140
tcaatggccc atctcgtctc tgaagcatct ttgctgtgag ctctagtccc cactgtcttg      1200
ctggaaaatg tggaggcccc actgcccact gcccagggca gcaatgccca taccacgtgg      1260
tcccagctcc gagcttgtcc tgaaaagggg gcaaagactg gaccctgagc ctgccaaggg      1320
gccacactcc tcccagggct ggggtctcca tgggcagccc ccacccacc cagaccagtt        1380
acactccct gtgccagagc agtgcagaca ggaccaggcc aggatgccca agggtcaggg       1440
gctggggatg ggtagccccc aaacagccct ttctggggga actggcctca acggggaagg      1500
```

-continued

```
gggtgaaggc tcttagtagg aaatcaggga gacccaagtc agagccaggt gctgtgcaga    1560
agctgcagcc tcacgtagaa ggaagaggct ctgcagtgga ggccagtgcc catccccggg    1620
tggcagaggc cccagcagag acttctcaat gacattccag ctggggtggc ccttccagag    1680
cccttgctgc ccgagggatg tgagcaggtg gccggggagg ctttgtgggg ccacccagcc    1740
ccttcctcac ctctctccat ctctcagact ccccagacag gccctggaac ccccccacct    1800
tctccccagc cctgctcgtg gtgaccgaag ggacaacgc caccttcacc tgcagcttct     1860
ccaacacatc ggagagcttc gtgctaaact ggtaccgcat gagccccagc aaccagacgg    1920
acaagctggc cgccttcccc gaggaccgca gccagcccgg ccaggactgc cgcttccgtg    1980
tcacacaact gcccaacggg cgtgacttcc acatgagcgt ggtcagggcc ggcgcaatg     2040 acagcggcac ctacctctgt ggggccatct ccctggcccc caaggcgcag atcaaagaga    2100
gcctgcgggc agagctcagg gtgacaggtg cggcctcgga ggccccgggg caggggtgag    2160
ctgagccggt cctggggtgg gtgtcccctc ctgcacagga tcaggagctc cagggtcgta    2220
gggcagggac cccccagctc cagtccaggg ctctgtcctg cacctgggga atggtgaccg    2280
gcatctctgt cctctagctc tggaagcacc ccagcccctc tagtctgccc tcaccctga    2340 ccctgaccct ccaccctgac cccgtcctaa ccctgacct ttgtgccctt ccagagagaa     2400
gggcagaagt gcccacagcc caccccagcc cctcacccag gccagccggc cagttccaaa    2460
ccctggtggt tggtgtcgtg ggcggcctgc tgggcagcct ggtgctgcta gtctgggtcc    2520
tggccgtcat ctgctcccgg gccgcacgag gtaacgtcat cccagcccct cggcctgccc    2580
tgccctaacc ctgctggcgg ccctcactcc cgcctcccct tcctccaccc ttccctcacc    2640
ccaccccacc taattgcatc gcattgtctg agtaggtgtc atagtactca tatgttgtgg    2700
tacaccagga aaggggacac tgatgcacct gtgcctgtgg caggccctac tcctcaattc    2760
attgtcctac caggaactcc ccgttagtaa atgggaaggg tgcccgtggg gatggaaagg    2820
ctggtgcttg cccatggtgt agatctcttc agtgcctgac acgcccctcc tgagcacaca    2880
aaacacacac acacacacac acacacacac acacacacac acacgagaa gagaaagatg      2940 gagagacaga gggaggacat tcctccacta gggaagatgg ctctgtagct gccctctaac    3000
ccaaactgtg tgtctcaaca gaggccagag gagctggaag caaggacgac actctggtga    3060
gtatgagttt tctttcttga gtgatctatc ccaggccacc cccaggtctt ggtacaggta    3120
gagagaccat ggggcctaca gggctagagc ctggagagcc cagctcccat tttctaccag    3180
gcccccagag ccatatcctg ttgttcctcc cagcagctga ccccactgtg tgtaccctg     3240 tcgtgtccaa cgtggtcacg acttgttttc ttctgtgcag agacaagggg caaaagtcaa    3300
attttggaat cctaaacccg ccaggaaaca tttaacgata gaaactgggc cagaaacacg    3360
aggctgcacc ctaaatatca agaagtcaat ggggagccta tggcctctgt gggttctgtg    3420
cctgggcagc tgttaggtca ggtcccagct tccatgactg aggtgaattt gctctaagaa    3480
gaaccccaaa tccagtgtca gtctggaaac ccagcatagg gaagggttga gattatggga    3540
tgcacacacc accccccaac tgactataac aatggctctt tcttctcccc cctcccctgc    3600
cccttgaaga aggaggagcc ttcagcagca cctgtcccta gtgtggccta tgaggagctg    3660
gacttccagg gacgagagaa gacaccagag ctccctaccg cctgtgtgca cacagaatat    3720
gccaccattg tcttcactga agggctgggt gcctcggc                            3758
```

<210> SEQ ID NO 37

```
<211> LENGTH: 22
<212> TYPE: DNA
<213> ORGANISM: Artificial Sequence
<220> FEATURE:
<223> OTHER INFORMATION: synthesized

<400> SEQUENCE: 37
acccctagcc tgggcctagt tc                                          22

<210> SEQ ID NO 38
<211> LENGTH: 26
<212> TYPE: DNA
<213> ORGANISM: Artificial Sequence
<220> FEATURE:
<223> OTHER INFORMATION: synthesized

<400> SEQUENCE: 38
tcggaattga atatttctag accagc                                      26

<210> SEQ ID NO 39
<211> LENGTH: 22
<212> TYPE: DNA
<213> ORGANISM: Artificial Sequence
<220> FEATURE:
<223> OTHER INFORMATION: synthesized

<400> SEQUENCE: 39
ttcttctggc ccatagagac ca                                          22

<210> SEQ ID NO 40
<211> LENGTH: 22
<212> TYPE: DNA
<213> ORGANISM: Artificial Sequence
<220> FEATURE:
<223> OTHER INFORMATION: synthesized

<400> SEQUENCE: 40
agctggttct ttccgcctca ga                                          22

<210> SEQ ID NO 41
<211> LENGTH: 23
<212> TYPE: DNA
<213> ORGANISM: Artificial Sequence
<220> FEATURE:
<223> OTHER INFORMATION: synthesized

<400> SEQUENCE: 41
ctggtgctgc tagtctgggt cct                                         23

<210> SEQ ID NO 42
<211> LENGTH: 24
<212> TYPE: DNA
<213> ORGANISM: Artificial Sequence
<220> FEATURE:
<223> OTHER INFORMATION: synthesized

<400> SEQUENCE: 42
cagcttgtgg taaacctgaa gtga                                        24

<210> SEQ ID NO 43
<211> LENGTH: 20
<212> TYPE: DNA
<213> ORGANISM: Artificial Sequence
<220> FEATURE:
<223> OTHER INFORMATION: synthesized

<400> SEQUENCE: 43
```

```
cacctaattg catcgcattg                                               20

<210> SEQ ID NO 44
<211> LENGTH: 20
<212> TYPE: DNA
<213> ORGANISM: Artificial Sequence
<220> FEATURE:
<223> OTHER INFORMATION: synthesized

<400> SEQUENCE: 44
tggctgaact gtagcctgca                                               20

<210> SEQ ID NO 45
<211> LENGTH: 20
<212> TYPE: DNA
<213> ORGANISM: Artificial Sequence
<220> FEATURE:
<223> OTHER INFORMATION: synthesized

<400> SEQUENCE: 45
ctagcaacag gagtataagt                                               20

<210> SEQ ID NO 46
<211> LENGTH: 20
<212> TYPE: DNA
<213> ORGANISM: Artificial Sequence
<220> FEATURE:
<223> OTHER INFORMATION: synthesized

<400> SEQUENCE: 46
catctttcga tccttctgca                                               20

<210> SEQ ID NO 47
<211> LENGTH: 20
<212> TYPE: DNA
<213> ORGANISM: Artificial Sequence
<220> FEATURE:
<223> OTHER INFORMATION: synthesized

<400> SEQUENCE: 47
atggcccaat atctatgtgt                                               20

<210> SEQ ID NO 48
<211> LENGTH: 20
<212> TYPE: DNA
<213> ORGANISM: Artificial Sequence
<220> FEATURE:
<223> OTHER INFORMATION: synthesized

<400> SEQUENCE: 48
agtccctgta cttggacatc                                               20

<210> SEQ ID NO 49
<211> LENGTH: 20
<212> TYPE: DNA
<213> ORGANISM: Artificial Sequence
<220> FEATURE:
<223> OTHER INFORMATION: synthesized

<400> SEQUENCE: 49
ccaaacttgt ggtgcttgca                                               20

<210> SEQ ID NO 50
<211> LENGTH: 20
<212> TYPE: DNA
```

```
<213> ORGANISM: Artificial Sequence
<220> FEATURE:
<223> OTHER INFORMATION: synthesized

<400> SEQUENCE: 50
ccatgttcac ttcttcacag                                               20

<210> SEQ ID NO 51
<211> LENGTH: 20
<212> TYPE: DNA
<213> ORGANISM: Artificial Sequence
<220> FEATURE:
<223> OTHER INFORMATION: synthesized

<400> SEQUENCE: 51
gccatccttt acttcctcgg                                               20

<210> SEQ ID NO 52
<211> LENGTH: 20
<212> TYPE: DNA
<213> ORGANISM: Artificial Sequence
<220> FEATURE:
<223> OTHER INFORMATION: synthesized

<400> SEQUENCE: 52
tttgggagaa gtcatgggct                                               20

<210> SEQ ID NO 53
<211> LENGTH: 20
<212> TYPE: DNA
<213> ORGANISM: Artificial Sequence
<220> FEATURE:
<223> OTHER INFORMATION: synthesized

<400> SEQUENCE: 53
aggtatttca gagggagaga                                               20

<210> SEQ ID NO 54
<211> LENGTH: 20
<212> TYPE: DNA
<213> ORGANISM: Artificial Sequence
<220> FEATURE:
<223> OTHER INFORMATION: synthesized

<400> SEQUENCE: 54
tgtgtgtata tgttgcgtgt                                               20

<210> SEQ ID NO 55
<211> LENGTH: 200
<212> TYPE: DNA
<213> ORGANISM: Artificial Sequence
<220> FEATURE:
<223> OTHER INFORMATION: synthesized

<400> SEQUENCE: 55
tggaaggggg atatatcgta aacagaacta acaaagacaa agaagtaagt gagagagagg    60
aactgggaaa caagcccgtg cacccgcgga taacttcgta taatgtatgc tatacgaagt   120
tatacttata ctcctgttgc taggaggtgg gtgggaagga agtgtagggt acaagcaagt   180
agagccttgc caaggaaagg                                              200

<210> SEQ ID NO 56
<211> LENGTH: 200
<212> TYPE: DNA
<213> ORGANISM: Artificial Sequence
```

<220> FEATURE:
<223> OTHER INFORMATION: synthesized

<400> SEQUENCE: 56

```
ggattaaagg cgtgcaccac catgcccagc ttccattttt attttattt tttgctacat    60
ctttcgatcc ttctgcaata acttcgtata atgtatgcta tacgaagtta tccgcggggg   120
ccctggtgct aagtccatca cttccacatt gctgcctgtc tgttagcttt aattcacagt   180
cactactctt ctgatcttgt                                               200
```

<210> SEQ ID NO 57
<211> LENGTH: 20
<212> TYPE: DNA
<213> ORGANISM: Artificial Sequence
<220> FEATURE:
<223> OTHER INFORMATION: synthesized

<400> SEQUENCE: 57

```
tccagccctt gacttgaatc                                                20
```

<210> SEQ ID NO 58
<211> LENGTH: 20
<212> TYPE: DNA
<213> ORGANISM: Artificial Sequence
<220> FEATURE:
<223> OTHER INFORMATION: synthesized

<400> SEQUENCE: 58

```
tcagaactgg gcagattccc                                                20
```

<210> SEQ ID NO 59
<211> LENGTH: 20
<212> TYPE: DNA
<213> ORGANISM: Artificial Sequence
<220> FEATURE:
<223> OTHER INFORMATION: synthesized

<400> SEQUENCE: 59

```
caatccaggt atttcagagg                                                20
```

<210> SEQ ID NO 60
<211> LENGTH: 20
<212> TYPE: DNA
<213> ORGANISM: Artificial Sequence
<220> FEATURE:
<223> OTHER INFORMATION: synthesized

<400> SEQUENCE: 60

```
gtgggaaaat gtgtcgtgca                                                20
```

<210> SEQ ID NO 61
<211> LENGTH: 20
<212> TYPE: DNA
<213> ORGANISM: Artificial Sequence
<220> FEATURE:
<223> OTHER INFORMATION: synthesized

<400> SEQUENCE: 61

```
tccagccctt gacttgaatc                                                20
```

<210> SEQ ID NO 62
<211> LENGTH: 20
<212> TYPE: DNA
<213> ORGANISM: Artificial Sequence
<220> FEATURE:

<223> OTHER INFORMATION: synthesized

<400> SEQUENCE: 62
tcagaactgg gcagattccc                                           20

<210> SEQ ID NO 63
<211> LENGTH: 20
<212> TYPE: DNA
<213> ORGANISM: Artificial Sequence
<220> FEATURE:
<223> OTHER INFORMATION: synthesized

<400> SEQUENCE: 63
caatccaggt atttcagagg                                           20

<210> SEQ ID NO 64
<211> LENGTH: 20
<212> TYPE: DNA
<213> ORGANISM: Artificial Sequence
<220> FEATURE:
<223> OTHER INFORMATION: synthesized

<400> SEQUENCE: 64
gtgggaaaat gtgtcgtgca                                           20

<210> SEQ ID NO 65
<211> LENGTH: 19
<212> TYPE: DNA
<213> ORGANISM: Artificial Sequence
<220> FEATURE:
<223> OTHER INFORMATION: synthesized

<400> SEQUENCE: 65
gagggcagct cttgcagac                                            19

METHOD FOR PREPARING CKO/KI ANIMAL MODEL BY USING CAS9 TECHNOLOGY

INCORPORATION OF SEQUENCE LISTING

This application contains a sequence listing submitted in Computer Readable Form (CRF). The CFR file containing the sequence listing entitled "PA440-0008_ST25", which was created on Mar. 25, 2021, and is 29,039 bytes in size. The information in the sequence listing is incorporated herein by reference in its entirety.

BACKGROUND

Technical Field

The present invention relates to a method for preparing an animal model by using Cas9 technology, in particular to a method for preparing a CKO/KI animal model.

Related Art

CKO/KI animal models have always been an important tool for studying gene function and screening drugs. However, the conventional preparation method requires a series of steps such as complex targeting vector construction, ES cell screening, and chimeric mouse breeding. The process is not only cumbersome and has high requirements on technology, but also is expensive and time-consuming, and the success rate is limited by many factors. Even for laboratories with relatively mature technology, it usually takes not less than one year to construct gene knockout rats and mice using conventional technology.

CRISPR/Cas9 is a technology that appeared in 2013 in which RNA directs Cas nuclease to perform specific DNA modification on targeted genes. In this system, a crRNA (CRISPR-derived RNA) combines with a tracrRNA (trans-activating RNA) through base pairing to form a double-stranded RNA. The tracrRNA/crRNA binary complex directs the Cas9 protein to cut a double-stranded DNA at a target locus of a crRNA guide sequence to produce a double-strand break (DSB). A cell repairs the broken double strands through nonhomologous or homologous DNA end joining (NHEJ: nonhomologous DNA end joining; HR, homology-directed repair), so as to achieve precise editing of the genome, such as: conditional gene knockout, gene knock-in, gene replacement, and point mutation.

The CRISPR/Cas9 technology is the fourth method that can be used for locus-specific construction of genetically modified animals following zinc finger nuclease (ZFN), ES cell targeting, TALEN technology, and the like, and has the characteristics of high efficiency, high speed, simplicity, economy, strong reproductive system transfer ability, and a very broad application prospect in animal model construction.

At present, when domestic and foreign laboratories and companies use the CRISPR/Cas9 technology, a Cas9-mRNA transcribed in vitro is generally transferred into embryos to express the Cas9 protein. However, the protein expression efficiency of the Cas9-mRNA transcribed in vitro in embryos is affected by the quality of an mRNA transcribed in vitro, which in turn affects the targeting efficiency. In addition, the targeting efficiency is also affected by the sgRNA cleavage efficiency, and the sgRNA activity score predicted by the website does not reflect the true cleavage efficiency of the sgRNA in the embryos. In addition, random insertion of a double-stranded targeting vector associated with the CRISPR/Cas9 technology cannot be ignored. However, a large number of studies have shown that using a single-stranded DNA as a repair template can reduce the random insertion rate.

This process has problems that the quality of the Cas9-mRNA is difficult to control, the cleavage efficiency of the sgRNA in vivo is unknown, and the double-stranded targeting vector is randomly inserted, which increase the cost and time of the experiment and limit wide application of the technology.

SUMMARY

In order to solve the above problems, the present invention replaces a Cas9-mRNA with a Cas9 protein expressed and purified in vitro, a large amount of Cas9 proteins can be prepared at one time, and the proteins can be applied to production after active cleavage. Meantime, in order to ensure the success rate of a project, first the sgRNA cleavage efficiency is tested with embryos to screen out high-efficiency sgRNA. In addition, we use a single-stranded DNA as a targeting vector, and the random insertion rate is greatly reduced.

The present invention aims to use the CRIPSR/Cas9 gene editing technology to realize multi-locus targeting of a genome by combining a protein obtained by in vitro expression and a high-efficiency sgRNA obtained through embryo screening, to cut multiple loci on a target gene, and to achieve the purpose of genome modification.

The present invention provides a method for preparing a CKO/KI animal model by using Cas9 technology, including: a Cas9 protein expressed and purified in vitro, a high-efficiency sgRNA screened by an sgRNA cleavage efficiency test on embryos and targeting a gene locus to be modified, and a single-stranded DNA targeting vector prepared according to model requirements are mixed and subjected to animal embryo injection and transplantation; F0 mice born after transplantation are subjected to genotype identification; F0 with the correct genotype identification are bred to obtain F1 mice; and the F1 mice are identified, analyzed and verified to obtain the CKO/KI animal model.

Specifically, the flow of the method of the present invention is as shown in FIG. 1, and includes the following steps:

step 1: preparation of a Cas9 protein with nuclease activity for subsequent steps, wherein the Cas9 protein is prepared by expression and purification in vitro;

step 2: screening of sgRNA (1) designing an sgRNA targeting a gene locus to be modified and preparing a transcription template;

(2) transcribing the sgRNA in vitro using a transcription kit, and the transcribed sgRNA being for later use;

(3) transferring the sgRNA from step (2) and the Cas9 protein from step 1 into mouse fertilized eggs by microinjection or electroporation, and testing the obtained embryos for sgRNA cleavage activity; and screening out the sgRNA with the best cleavage activity for later use;

step 3: design and construction of targeting vector scheme developing a model production scheme according to needs, and designing the targeting vector scheme based on the model production scheme, preparing the vector according to the targeting vector scheme, and using a single-stranded DNA as the targeting vector;

step 4: embryo injection and transplantation mixing the targeting vector constructed correctly in step 3, the Cas9 protein from step 1, and the sgRNA with the best cleavage activity obtained in step 2, and carrying out embryo injection and transplantation by using the mixed sample; and step 5: marking mice born after transplantation as F0 and carrying out the genotype identification of F0; breeding sexually mature F0 with the correct genotype identification, and marking the offspring mice thereof as F1; analyzing and verifying the F1 mice, and the F1 mice with the correct genotype verification being the prepared CKO/KI animal model.

In step 1 of the method of the present invention, the cleavage activity of Cas9-protein can be judged according to the cleavage ratio, and the Cas9 protein with a cleavage ratio of 50% or above can be used in subsequent steps.

The step (1) of step 2 may specifically be: an sgRNA targeting a modified locus is designed through a design website, an sgRNA transcription vector is constructed, and an in vitro transcription template is prepared by digestion and purification of the transcription vector.

The step (2) of step 2 may specifically be: the RNA is transcribed according to the operation manual of an RNA in vitro transcription kit (NEB #E2050S), and the RNA is purified according to the operation manual of an RNA purification kit (Ambion AM1908).

Reagent I: HiScribe™ T7 Quick High Yield RNA Synthesis Kit (NEB #E2050S)

Reagent II: AmbionMEGAclear kit (AmbionAM1908)

In vitro transcription of the RNA is carried out according to the operation manual of the HiScribe™ T7 Quick High Yield RNA Synthesis Kit (NEB #E2050S), and RNA purification is carried out according to the operation manual of the AmbionMEGAclear kit (Ambion AM1908).

The sgRNA cleavage activity test on the obtained embryos in the step (3) of step 2 is specifically: PCR identification of the obtained embryos is carried out to confirm the sgRNA cleavage activity.

The beneficial effects of the present invention are embodied in: the present invention replaces a Cas9-mRNA with a Cas9 protein expressed and purified in vitro, and the preparation of multiple models can be satisfied with preparation at one time. The technical efficiency is high, and the experimental cost is lowered. The sgRNA cleavage efficiency is tested with the embryos to screen out high-efficiency sgRNA, and the success rate of the project is ensured. In addition, we use the single-stranded DNA as the targeting vector, and the random insertion rate is greatly reduced. The technical process is complete, multiple technical services can be carried out at the same time, and different customized needs are met. The problems of difficult control of Cas9-mRNA quality, unknown sgRNA cleavage efficiency in vivo, random insertion of double-stranded targeting vectors, and the like are solved, and the experimental cost is reduced.

Note: the number in the figure represents the mouse number; B6 is a negative control, and is the mouse genomic DNA (MouseGRC38/mm10); N is a blank control, the control without a template; P is a positive plasmid control; TRANS2K PLUS II strip: 8000 bp\5000 bp\3000 bp\2000 bp\1000 bp\750 bp\500 bp\250 bp\100 bp.

Figure 4:
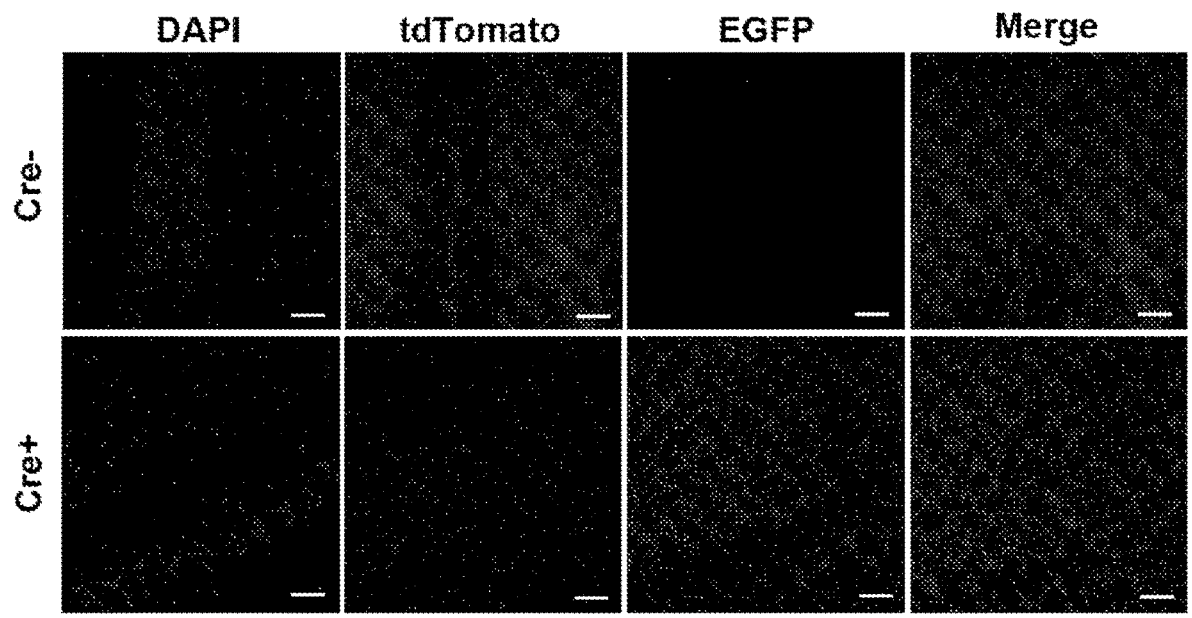

FIG. 4 is a detection image of brain cells in model mice. Among them: Cre− is the abbreviation of rosa26-loxP-tdtomato-loxP-GFP mice; Cre+ is the abbreviation of offspring mice of rosa26-loxP-tdtomato-loxP-GFP and Nes-Cre. Cre− and Cre+ mice are both 15.0-week-old male mice, and the diagram is fluorescence pictures under a 200× microscope (Scale bar 50 μM).

Figure 5:
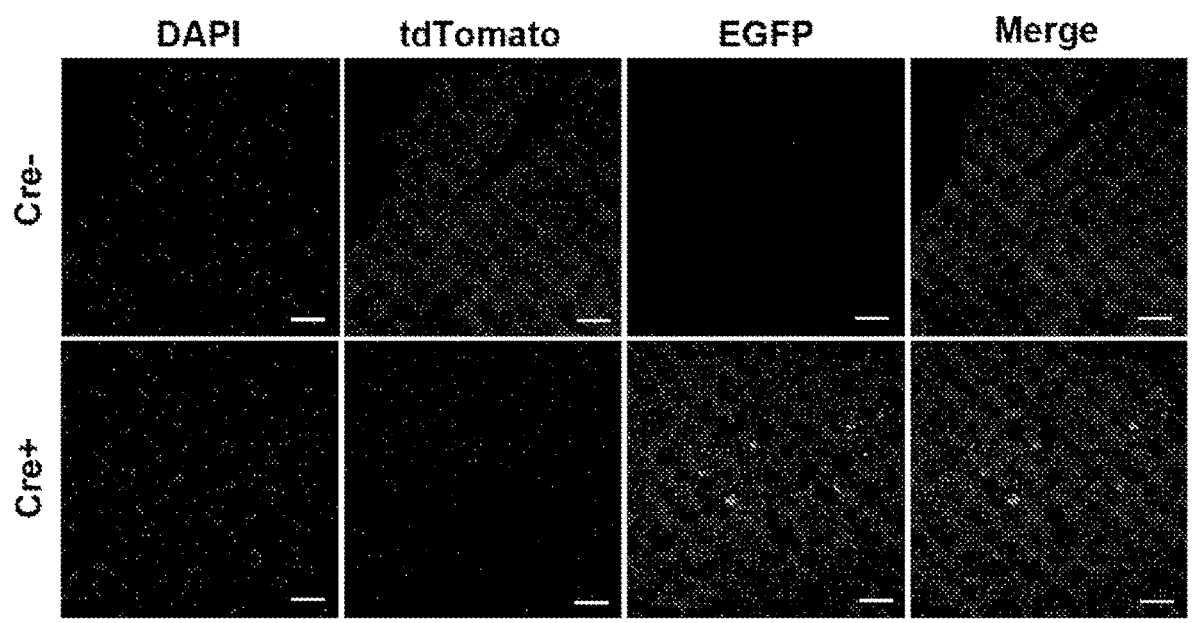

FIG. 5 is a detection image of spinal cord cells in model mice. Among them: Cre− is the abbreviation of rosa26-loxP-tdtomato-loxP-GFP mice; Cre+ is the abbreviation of offspring mice of rosa26-loxP-tdtomato-loxP-GFP and Nes-Cre. Cre− and Cre+ mice are both 15.0-week-old male mice, and the diagram is fluorescence pictures under a 200× microscope (Scale bar 50 μM).

Figure 6:
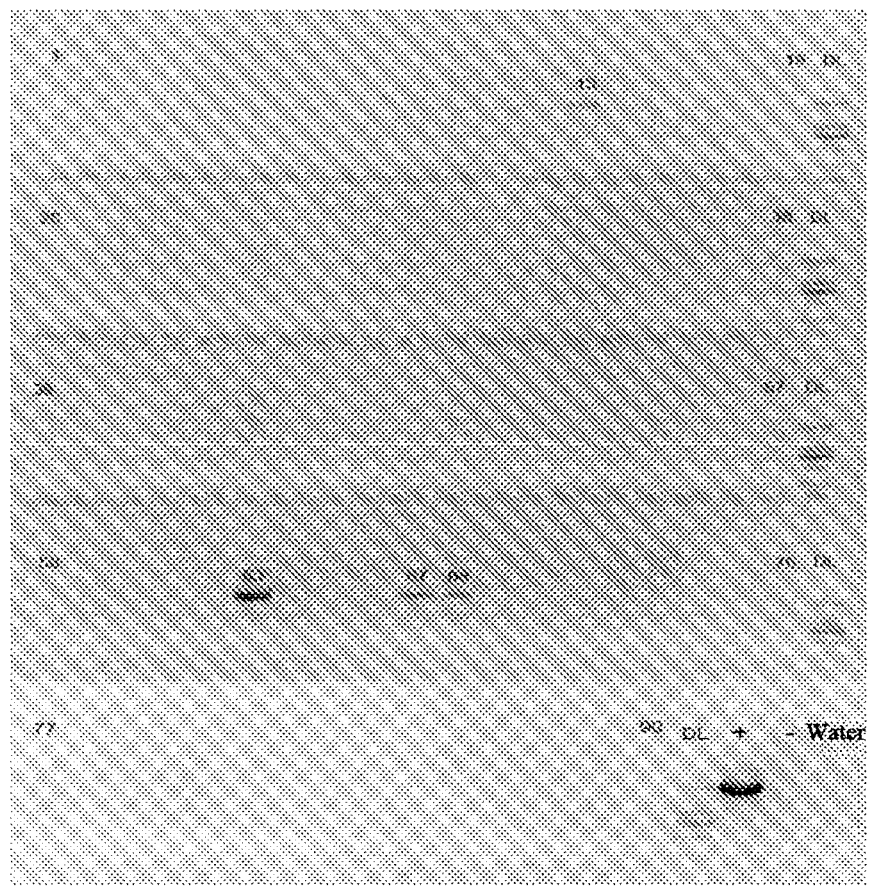
Figure 6:
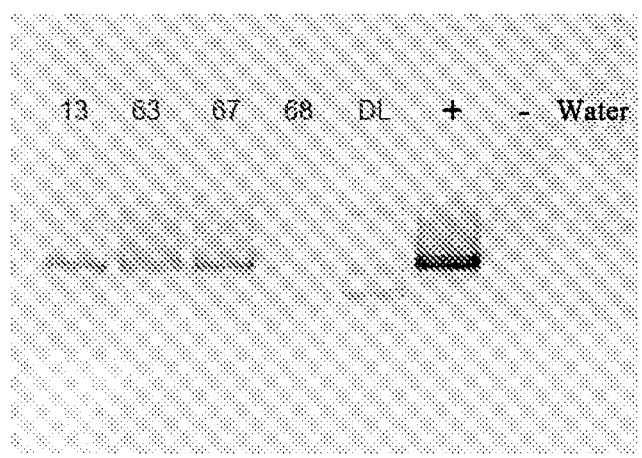

FIG. 6 shows the Cas9-mRNA+Erbb2ip donor targeting identification result. A. 5-end identification of Cas9-mRNA+Erbb2ip donor targeting; B. 3-end identification of Cas9-mRNA+Erbb2ip donor targeting; the number in the figure represents the embryo number; "-" or "B6" is a negative control, and is the embryonic genomic DNA; "Blank" and "Water" are blank controls, the controls without templates; the sizes of Marker DL strips are respectively: 2000 bp/1000 bp/750 bp/500 bp/250 bp/100 bp.

Figure 7:
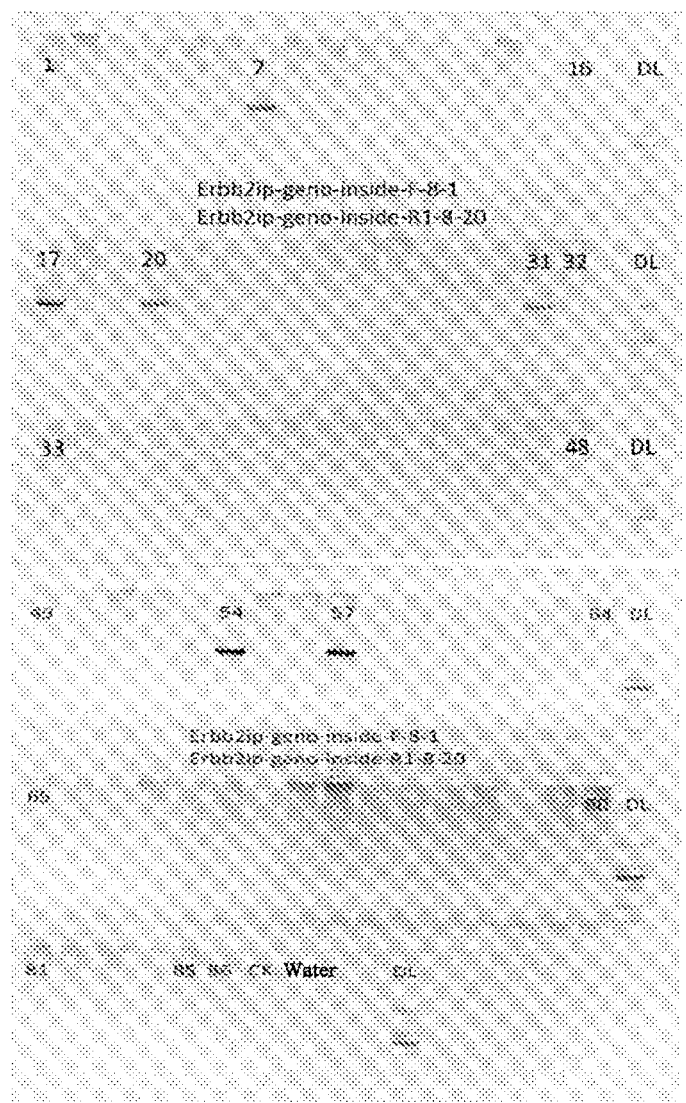
Figure 7:
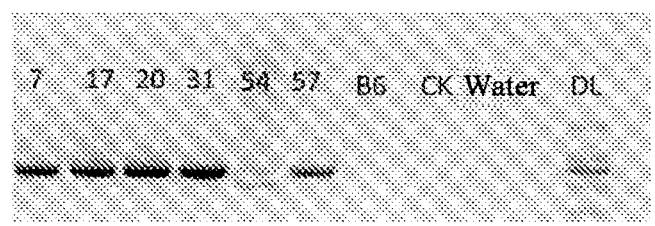

FIG. 7 shows the Cas9-Protein+Erbb2ip donor targeting identification result. A. 5-end identification of Cas9-Protein+Erbb2ip donor targeting; B. 3-end identification of Cas9-Protein+Erbb2ip donor targeting; the number in the figure represents the embryo number; "-" or "B6" is a negative control, and is the embryonic genomic DNA; "Blank" and "Water" are blank controls, the controls without templates; the sizes of Marker DL strips are respectively: 2000 bp/1000 bp/750 bp/500 bp/250 bp/100 bp.

Figure 8:
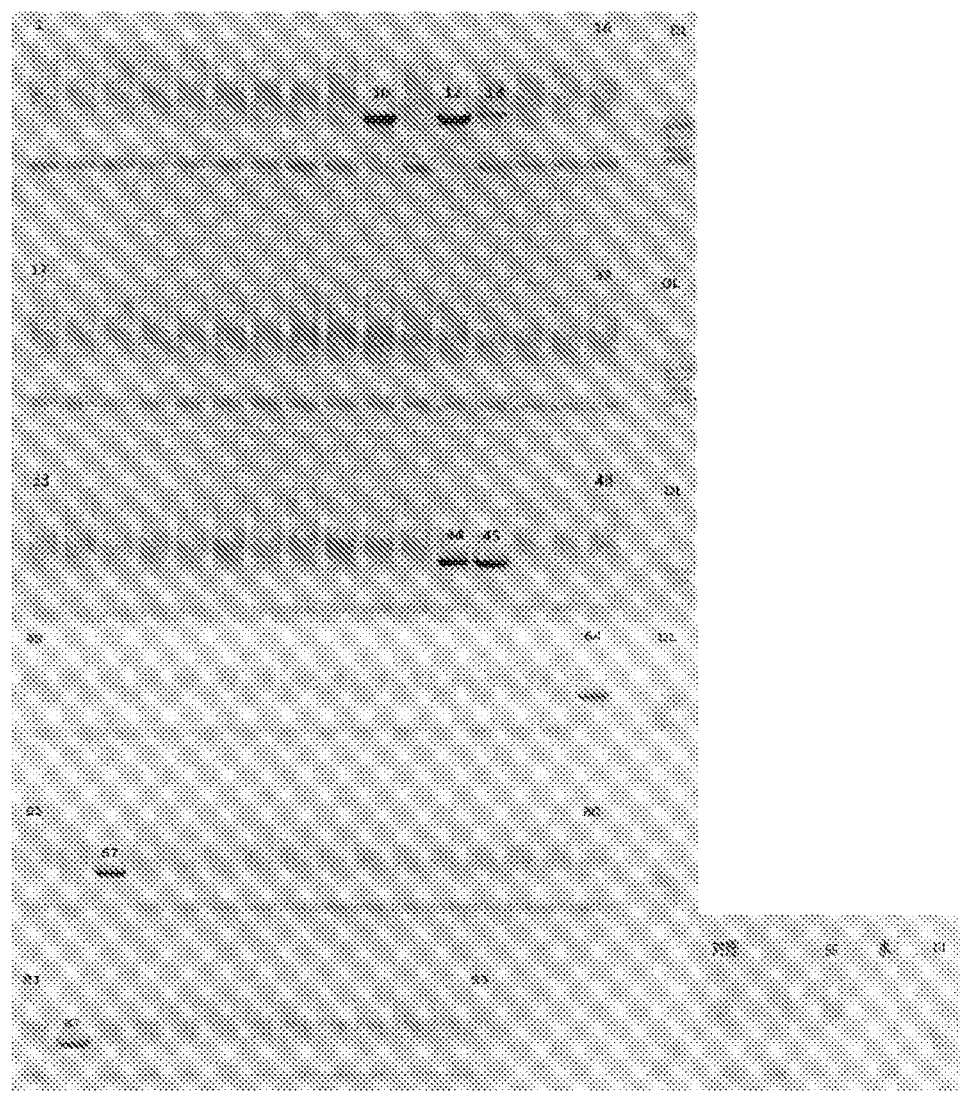
Figure 8:
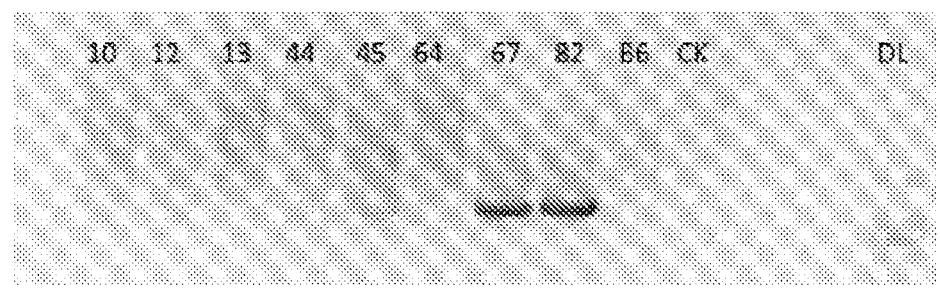

FIG. 8 shows the Cas9-mRNA+Ly101 donor targeting identification result. A. 5-end identification of Cas9-mRNA+Ly101 donor targeting; B. 3-end identification of Cas9-mRNA+Ly101 donor targeting; the number in the figure represents the embryo number; "-" or "B6" is a negative control, and is the embryonic genomic DNA; "Blank" and "Water" are blank controls, the controls without templates; the sizes of Marker DL strips are respectively: 2000 bp/1000 bp/750 bp/500 bp/250 bp/100 bp.

Figure 9:
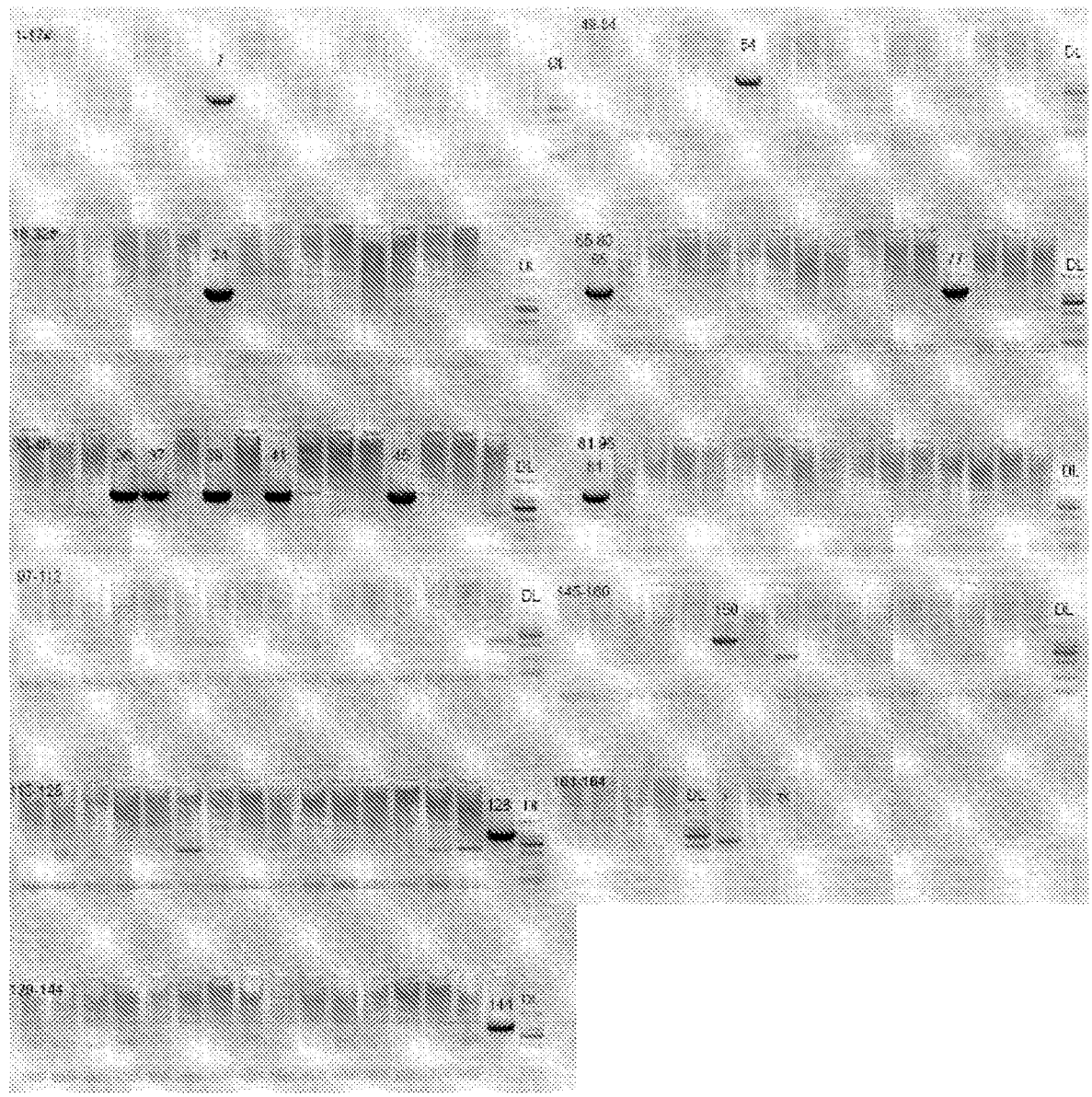

FIG. 9 shows the Cas9-Protein+Ly101 donor targeting identification result. A. 5-end identification of Cas9-Protein+Ly101 donor targeting; B. 3-end identification of Cas9-Protein+Ly101 donor targeting; the number in the figure represents the embryo number; "-" or "B6" is a negative control, and is the embryonic genomic DNA; "Blank" and "Water" are blank controls, the controls without templates; the sizes of Marker DL strips are respectively: 2000 bp/1000 bp/750 bp/500 bp/250 bp/100 bp.

Figure 10:
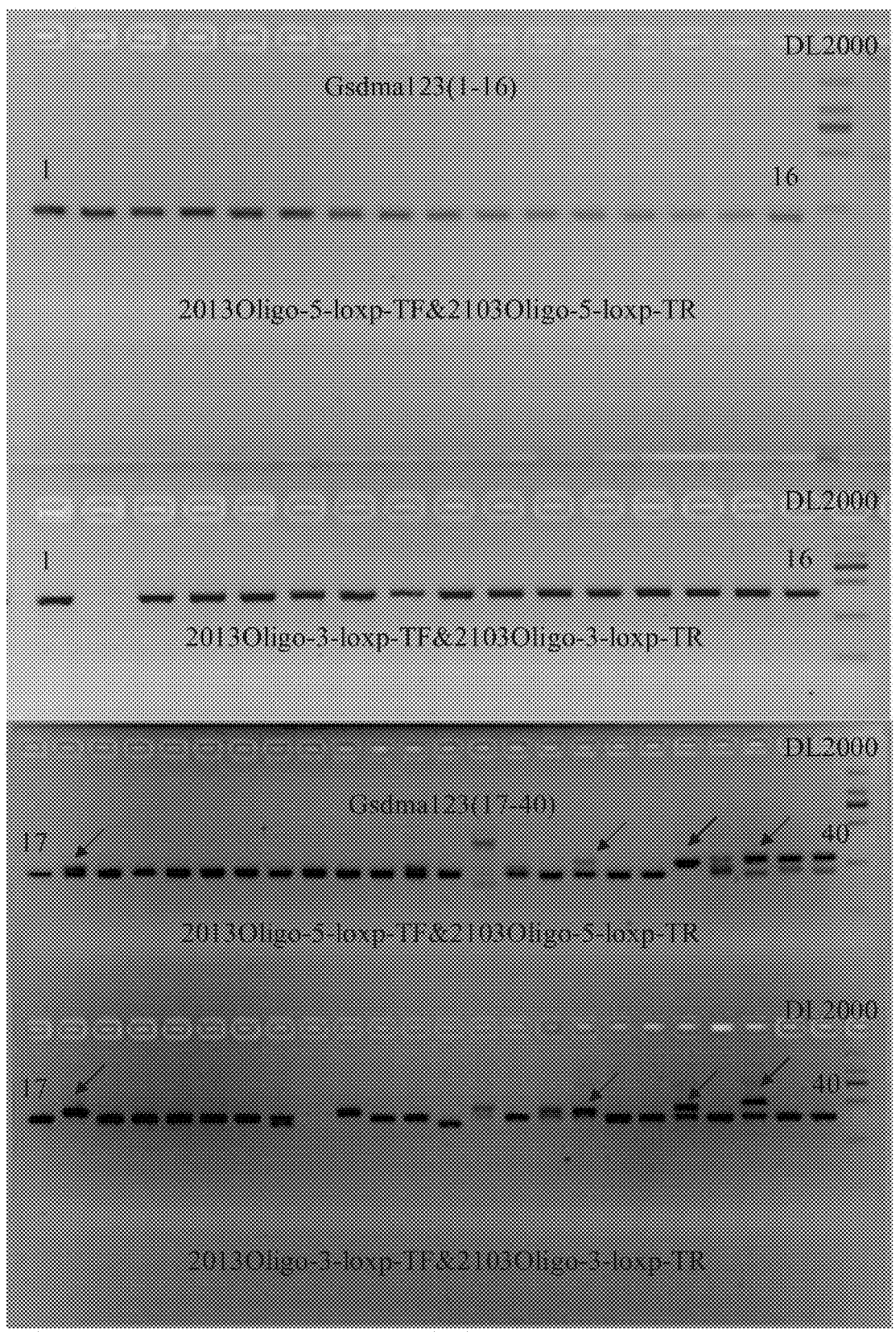
Figure 10:
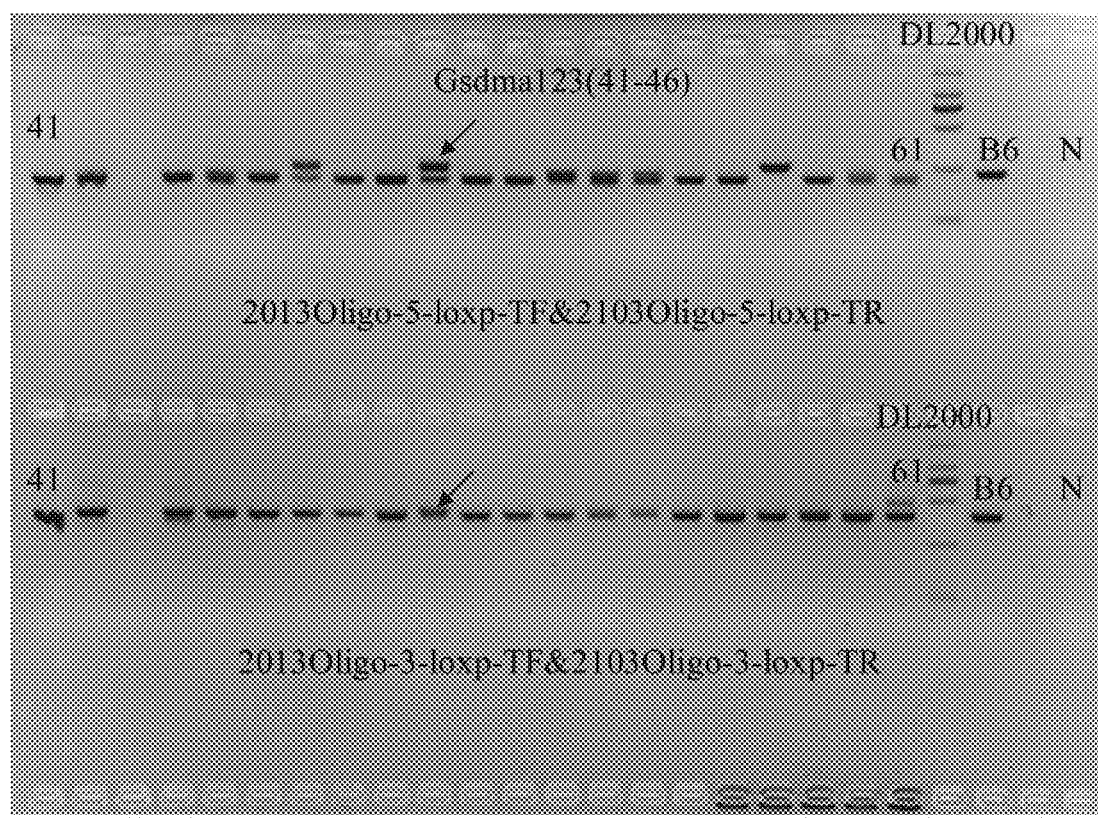

FIG. 10 is the electrophoresis result of F0 genotype identification. The number in the figure represents the mouse number; B6 is a negative control, and is the mouse genomic DNA; N is a blank control, the control without a template; DL2000 strips: 2000 bp\1000 bp\750 bp\500 bp\250 bp\100 bp.

Figure 11:

FIG. 11 is the electrophoresis result of genotype identification of F1 mice. The number in the figure represents the mouse number; B6 is a negative control, and is the mouse genomic DNA; N is a blank control, the control without a template; DL2000 strips: 2000 bp\1000 bp\750 bp\500 bp\250 bp\100 bp.

DETAILED DESCRIPTION

Example 1: a method for preparing a Nes-Cre animal model based on Cas9 technology is realized by the following steps.

Step 1: a Cas9 protein was prepared. The Cas9 protein was prepared by expression and purification in vitro, and the activity thereof was tested. The protein with nuclease activity can be used for subsequent experiments. A commercial Cas9 active protein may also be purchased.

Reagent I: PrimeSTAR Max DNA Polymerase (Takara R045A)

Reagent II: Gel/PCR DNA Fragments Extraction Kit (Geneaid DF100)

Reagent III: NEBuffer3.1 (10×) (NEB #B7203S)

Reagent IV: 10× Loading Buffer (Takara 9157)

1) A C57BL/6 genome (MouseGRCm38/mm10) was used as a template, and PCR amplification was performed according to the operation manual of PrimeSTAR Max DNA Polymerase (Takara R045A). The primer information is as follows:

| Primer name | Primer sequence | Stripe size |
| --- | --- | --- |
| F | TGGCTCACAAACATCCGTAATGA (SEQ ID NO. 1) | 685 bp |
| R | CAGTCAGTAAACGGATCAAAGCT (SEQ ID NO. 2) | |

The PCR system is as follows:

| Reagent | Volume (μl) | Specification |
| --- | --- | --- |
| 2x PrimerStarMax | 25 | |
| ddH$_2$O | 22 | |
| F | 1 | 10 μM |
| R | 1 | 10 μM |
| C57BL/6 genome DNA | 1 | |

The PCR procedure is as follows:

| PCR procedure | | | |
| --- | --- | --- | --- |
| Seg. | Temp. | Time | Cycle |
| 1 | 98° C. | 3 min | |
| 2 | 98° C. | 10 s | |
| 3 | 58° C. | 10 s | |
| 4 | 72° C. | 40 s | 2-4, 35 |
| 5 | 72° C. | 3 min | |
| 6 | 4° C. | hold | |

2) The amplified target fragment was detected by agarose gel electrophoresis, and the PCR product was recovered through the operation manual of a Gel/PCR DNA Fragments Extraction Kit (Geneaid DF100). The PCR product concentration measured by an ultraviolet spectrophotometer is 76.95 ng/μl (GD 260/280=1.85), and the PCR product sequence is as set forth in SEQ ID NO.10.

A sample addition system is as follows:

| Group | Experimental group | Control group |
| --- | --- | --- |
| PCR product (200 ng) (SEQ ID NO. 10) | 2.6 μl | 2.6 μl |
| Cas9-Protein | 2 μl | — |
| sgRNA-1 | 1 μl | 1 μl |
| NEBuffer 3.1 (10x) | 3 μl | 3 μl |
| ddH$_2$O | 21.4 μl | 23.4 μl |

The order of sample addition is: water, Buffer, Cas9-Protein, sgRNA-1, and PCR recovery product. After the sample was added, the sample was mixed well using a pipette. After mixing, the sample was incubated at 37° C. for 1 h, heated at 72° C. for 10 min, and kept at 4° C.

The sgRNA-1 sequence is GAGGGCAGCTCTTGCAGAC (SEQ ID NO.65).

Figure 1:
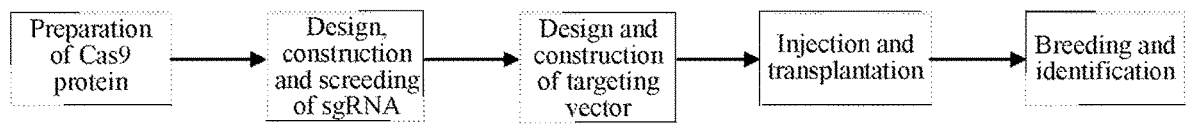
FIG. 1 is a flow chart of application of Cas9 technology to preparation of an animal model.
Figure 2:
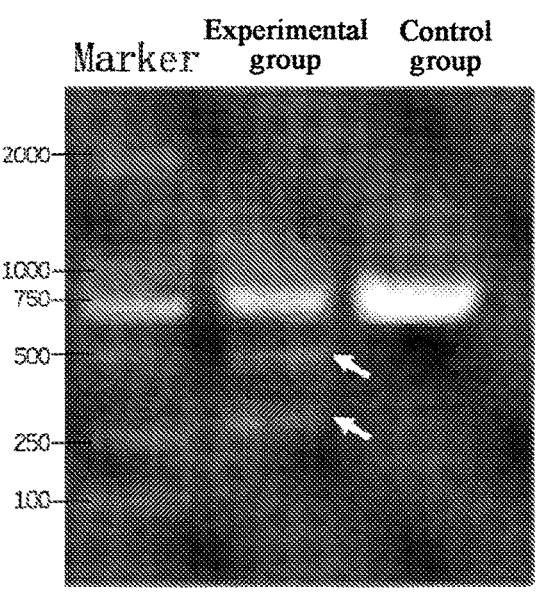
FIG. 2 is an electropherogram of cleavage activity test of Cas9-protein, wherein the Marker is Marker DL 2000.

After completion, the sample was taken out immediately and placed on ice to cool for 5 min. 3.4 μl of 1% SDS was added, and 4 μl of 10× loading buffer was added after water bath action at 55° C. for 10 min. Agarose gel electrophoresis was performed, and the electrophoresis result is as shown in FIG. 2. In the system with Cas9-protein and the corresponding sgRNA, obvious cleavage can be seen, and the control group has no cleavage. The cleavage activity of Cad-protein is judged according to the ratio of cleavage. The Cas9 protein with a cleavage ratio of 50% or above can be used for subsequent projects and experiments.

Step 2: screening of sgRNA (1) The sgRNA targeting a knock-in locus was designed and an sgRNA transcription template was prepared.

The sgRNA targeting the KI locus was designed using a Cas9sgRNA design website crispr.mit.edu, and a corresponding Oligo was ordered to construct the sgRNA.

The sgRNA sequences are as follows:

| sgRNA name | Sequence | PAM |
| --- | --- | --- |
| Nes-Cre-S1 | GAACACTAGTGCACTTATCC (SEQ ID NO. 3) | TGG |
| Nes-Cre-S2 | CTGAGCCAACAGTGGTAGTA (SEQ ID NO. 4) | AGG |
| Nes-Cre-S3 | AACACTAGTGCACTTATCCT (SEQ ID NO. 5) | GGG |
| Nes-Cre-S4 | CCAACAGTGGTAGTAAGGTA (SEQ ID NO. 6) | AGG |
| Nes-Cre-S5 | TGGTAGTAAGGTAAGGGC (SEQ ID NO. 7) | AGG |
| Nes-Cre-S6 | CCAACAGTGGTAGTAAGGTAA (SEQ ID NO. 8) | GGG |
| Nes-Cre-S7 | TCTGGAAAAAGCAGTCCCAC (SEQ ID NO. 9) | TGG |

Forward an reverse pnmers were annealed to orm double strands, an then the double strands were ligated with a pUC57-T7 universal vector singly digested with Bsal to construct a transcription vector containing the sgRNA sequence. The sequencing verification by a professional sequencing company showed that the target plasmid was obtained.

The obtained target plasmid was digested at 37° C. overnight. After completion, agarose gel electrophoresis was performed. The target strips were cut for gel recovery, and a final product obtained was recovered as a transcription template.

(2) All sgRNAs were transcribed in vitro using a transcription kit, and the transcribed sgRNAs were for later use.

Reagent I: HiScribe™ T7 Quick High Yield RNA Synthesis Kit (NEB #E2050S)

Reagent II: AmbionMEGAclear kit (Ambion AM1908)

In vitro transcription of the RNAs was carried out according to the operation manual of a HiScribe™ T7 Quick High Yield RNA Synthesis Kit (NEB #E2050S), and RNA purification was carried out according to the operation manual of an AmbionMEGAclear kit (AmbionAM1908).

(3) The sgRNA and Cas9 protein were transferred into mouse fertilized eggs by microinjection or electroporation according to the method in the "Mouse Embryo Operation Experiment Manual". The obtained embryos were tested for sgRNA cleavage activity by nested PCR. The PCR products were sequenced and verified by a professional sequencing company, and the Nes-Cre-S2 with high efficiency of a knock-in locus was obtained by screening.

The PCR system is as follows:

| Reagent | Volume (μl) | Specification |
|---|---|---|
| 10x Buffer | 2.5 | |
| ddH₂O | 17.75 | |
| primerF | 0.5 | 10 μM |
| primerR | 0.5 | 10 μM |
| Mg2+ | 2 | 25 mM |
| dNTPs | 0.5 | 10 mM each |
| Taq | 0.25 | 5 U/μl |
| Template | 1 | |

PCR primers are as follows:

| No. | Primer name | Primer sequence | Stripe size | Remarks |
|---|---|---|---|---|
| 1 | Nes-Cre-outF 1 | ggcacaatgttaatc cagcctgactccaa (SEQ ID NO. 12) | 923 bp | First round PCR |
|  | Nes-Cre-outR 1 | gcttgccttgaacttc actatatagggctta (SEQ ID NO. 13) | | |
| 2 | Nes-Cre-inF 1 | ggggccataaatgcta ttttaattccact (SEQ ID NO. 14) | 647 bp | Second round PCR |
|  | Nes-Cre-inR 1 | ccaccttcttcagtta gcttctgtacac (SEQ ID NO. 15) | | |

The PCR procedure is as follows:

| PCR procedure | | | |
|---|---|---|---|
| Seg. | Temp. | Time | Cycle |
| 1 | 95° C. | 5 min | |
| 2 | 95° C. | 30 s | |
| 3 | 65° C. | 30 s | 2-4, 35x |
| 4 | 72° C. | 45 s | |
| 5 | 95° C. | 5 min | |
| 6 | 72° C. | 5 min | |

The sgRNA cleavage efficiency is as follows:

| sgRNA name | Cleavage efficiency (Range: 0-100%) | Predicted Efficiency (Range: 0-100) |
|---|---|---|
| Nes-Cre-S1 | 45 | 37 |
| Nes-Cre-S2 | 85 | 40 |
| Nes-Cre-S3 | 68 | 50 |
| Nes-Cre-S4 | 50 | 45 |
| Nes-Cre-S5 | 30 | 53 |
| Nes-Cre-S6 | 10 | 45 |
| Nes-Cre-S7 | 60 | 56 |

There is a difference between the sgRAN activity score predicted by the website and the sgRNA cleavage efficiency of embryos. We chose the Nes-Cre-S2, with a higher cleavage efficiency in embryo testing, as the sgRNA for targeting.

Step 3: a targeting vector containing a knock-in locus homologous arm, a Nestin promoter, Cre CDS, and HGH-polyA originals was designed and constructed. The above fragments were ligated with a PMID18T universal vector through a NEBuilder® HiFi DNA Assembly Master Mix (E2621 S) kit. Finally, the Nes-Cre targeting vector was obtained. The sequence of the Nes-Cre targeting vector is as set forth in SEQ ID NO. 11.

Step 4: embryo injection and transplantation

The correctly constructed targeting vector Nes-Cre, the Cas9 protein and the Nes-Cre-S2sgRNA were mixed, and the mixed injection sample was provided to the injection personnel for carrying out embryo injection and transplantation.

Step 5: the mice born after transplantation were marked as F0, and sexually mature positive F0 with correct genotype identification was bred. The offspring mice were marked as F1, and theF1 mice were analyzed and verified.

The PCR system for genotype identification of F1 mice is as follows:

| Reagent | Volume (μl) | Specification |
|---|---|---|
| 2x PrimerStarMax | 25 | |
| ddH₂O | 22 | |
| F | 1 | 10 μM |
| R | 1 | 10 μM |
| Template | 1 | |

PCR primers are as follows:

| No. | Primer name | Primer sequence | Stripe size | Remarks |
|---|---|---|---|---|
| 1 | Nes-Cre-tF2 | ATGCCCACCAAAGTC ATCAGTGTAG (SEQ ID NO. 16) | 1527 bp | 5-end |
|  | Nes-Cre-tR1 | CCTTAACTCGGGTTG CCAGGT (SEQ ID NO. 17) | | |
| 2 | Nes-Cre-3tF2 | CCTCCTCTCCTGACT ACTCCCAGTC (SEQ ID NO. 18) | 3072 bp | 3-end |
|  | Nes-Cre-tR2 | TCACAGAAACCATAT GGCGCTCC (SEQ ID NO. 19) | | |

The PCR procedure is as follows:

| Touch down PCR procedure (Touch down Cycling) | | | | |
|---|---|---|---|---|
| Seg. | Temp. | Time | Cycle | ±Temp/cycle |
| 1 | 95° C. | 5 min | | |
| 2 | 98° C. | 30 s | | |
| 3 | 65° C. | 30 s | 2-4, 20x | −0.5 |
| 4 | 72° C. | 45 s | | |
| 5 | 98° C. | 30 s | | |
| 6 | 55° C. | 30 s | | |
| 7 | 72° C. | 45 s | 5-7, 20x | |
| 8 | 72° C. | 5 min | | |
| 9 | 10° C. | hold | | |

Figure 3:
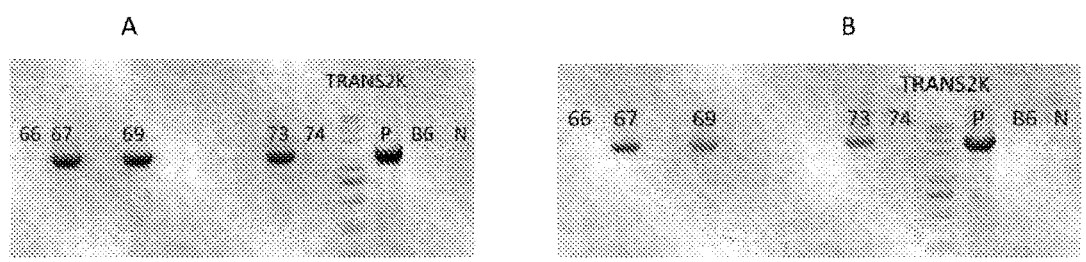
FIG. 3 shows the genotype identification result of Nes-CreF1 mice. A: 5-end identification result; B: 3-end identification result.

The genotype identification result of the Nes-CreF1 mice is as shown in FIG. 3. The PCR products (target fragments) were sequenced and verified by a professional sequencing company, and 3 positive F1 mice were screened.

Example 2: Functional Analysis of Nes-Cre Model Mice

Under the action of the nestin-promoter, the model expresses a Cre enzyme specifically in the central and peripheral nervous system, and can be used as a Cre tool mouse for specific induction of LoxP recombination in the central and peripheral nervous system. The positive F1 mice obtained in Example 1 were mated with fluorescent reporter gene tool mice (rosa26-loxP-tdtomato-loxP-GFP) to breed. Rosa26-loxP-tdtomato-loxP-GFP tool mice expressed red fluorescence, and when they were mated with Cre recombinase-expressing mice, the offspring expressed green fluorescence because tdTtomato was missing in cells expressing ere. By observing frozen sections, the expression of green fluorescence could be observed to confirm the expression of ere protein in the central and peripheral nervous system, so as to perform functional analysis of the model.

By observing the frozen sections, it can be seen that in the offspring mice bred by mating the fluorescent reporter gene tool mice with the Nes-Cre mice, the tdTomato and stop originals in the brain and spinal cord cells were cut, and the brain and spinal cord cells could express green fluorescent EGFP. Other cells that could not express cre still expressed red fluorescence. The detection diagrams are as shown in FIG. 4 and FIG. 5.

Example 3: a comparative test of the effects of the Cas9-mRNA and the Cas9 protein on the sgRNA-2 cleavage efficiency proves that the sgRNA cleavage efficiency of the Cas9-Protein+sgRNA combination is higher than that of the Cas9-mRNA+sgRNA combination.

Step 1: the sgRNA-2 was used as the sgRNA for testing, and the sequence of the sgRNA-2 is as follows:

The sequence of the sgRNA-2 is as follows:

| sgRNA name | Sequence | PAM |
| --- | --- | --- |
| sgRNA-2 | AGTCTTCTGGGCAGGCTTAA (SEQ ID NO. 20) | AGG |

Step 2: the sgRNA and the Cas9 system were transferred into mouse fertilized eggs by microinjection or electroporation according to the method in the "Mouse Embryo Operation Experiment Manual". The obtained embryos were tested for sgRNA cleavage activity by nested PCR. The PCR products were sequenced and verified by a professional sequencing company, and the result shows that the cleavage efficiency of the Cas9-Protein+sgRNA is better than that of the Cas9-mRNA+sgRNA.

The PCR system is as follows:

| Reagent | Volume (μl) | Specification |
| --- | --- | --- |
| 10x Buffer | 2.5 | |
| ddH$_2$O | 16.75 | |
| primerF | 1 | 10 μM |
| primerR | 1 | 10 μM |
| Mg2+ | 2 | 25 mM |
| dNTPs | 0.5 | 10 mM each |
| Taq | 0.25 | 5 U/μl |
| Template | 1 | |

PCR primers are as follows:

| Primer No. | Primer name | Primer sequence | Stripe size | Remarks |
| --- | --- | --- | --- | --- |
| 1 | sgRNA-2-outF | AGACAGCCGGGTACGAGTCGTGA (SEQ ID NO. 21) | 1938 bp | First round PCR |
| | sgRNA-2-outR | CAGCCTGGCAATATGTAAGATACATCAG (SEQ ID NO. 22) | | |
| 2 | sgRNA-2-inF | GTGCAAGCACGTTTCCGACTTG (SEQ ID NO. 23) | 882 bp | Second round PCR |
| | sgRNA-2-inR | CTGGTTTCATGAGTCATCAGACTTCTA (SEQ ID NO. 24) | | |

The PCR procedure is as follows:

| Seg. | Temp. | Time | Cycle |
| --- | --- | --- | --- |
| 1 | 95° C. | 5 min | |
| 2 | 95° C. | 30 s | |
| 3 | 58° C. | 30 s | 2-4, 35x |
| 4 | 72° C. | 1 kb/min | |
| 5 | 72° C. | 5 min | |
| 6 | 10° C. | hold | |

The sgRNA cleavage efficiency is as follows:

| Name | Cleavage efficiency |
| --- | --- |
| Cas9-mRNA + sgRNA-2 | 14.3% |
| Cas9-Protein + sgRNA-2 | 70% |

Example 4: a comparative test of the effects of the Cas9-mRNA and the Cas9 protein on the Erbb2ip gene targeting efficiency proves that the targeting efficiency of the Cas9-Protein+sgRNA+Donor combination is higher than that of the Cas9-mRNA+sgRNA+Donor combination.

Step 1: the sgRNA corresponding to the Erbb2ip gene was used, and the sequence of the sgRNA is as follows:

| sgRNA name | Sequence | PAM |
| --- | --- | --- |
| Erbb2ip-5S | TCAAGGGATGCTCTTCAATA (SEQ ID NO. 25) | TGG |
| Erbb2ip-3S | GAGAGGCCCAATGCCCAACG (SEQ ID NO. 26) | TGG |

An Erbb2ip gene targeting donor was used, and the targeting donor sequence is as set forth in SEQ ID NO.27.

The sgRNA, donor, and Cas9 system were transferred into mouse fertilized eggs by microinjection or electroporation according to the method in the "Mouse Embryo Operation Experiment Manual", and the obtained embryos were tested for the gene targeting efficiency by nested PCR. The result shows that the Cas9-Protein+sgRNA+Donor combination has higher targeting efficiency than the Cas9-mRNA+sgRNA+Donor combination.

The specific targeting efficiency result is as follows:

| Name | Cleavage efficiency |
| --- | --- |
| Cas9-mRNA + Erbb2ip donor | 3.33% (3/90) |
| Cas9-Protein + Erbb2ip donor | 7.05% (6/85) |

The PCR system is as follows:

| Reagent | Volume (μl) | Specification |
| --- | --- | --- |
| 10x Buffer | 2.5 | \ |
| ddH$_2$O | 17.75 | \ |
| PrimerF | 0.5 | 10 μM |
| PrimerR | 0.5 | 10 μM |
| Mg2+ | 2 | 25 mM |
| dNTPs | 0.5 | 10 mM each |
| Taq | 0.25 | 5 U/μl |
| Template | 1 | ≈100 ng/μl |

PCR primers are as follows:

| No. | Primer name | Primer sequence | Stripe size | Primer description |
| --- | --- | --- | --- | --- |
| 1 | Erbb2ip-geno-outside-F-8-1 | GGAACCATTAGATTT AACCAGAC (SEQ ID NO. 28) | 2663 bp | First round |
| | Erbb2ip-geno-outside-R-8-1 | CTGTTTACAAAGTCT AAGGTGTG (SEQ ID NO. 29) | | |
| 2 | Erbb2ip-geno-inside-F-8-1 | TTGTTTATTACAGTC TGTATCCC (SEQ ID NO. 30) | KI: 2032 bp Wt: none | Detection of 5-end |
| | Erbb2ip-geno-inside-R1-8-20 | AGATGTTGGAGCTCG ATATCATAAC (SEQ ID NO. 31) | | |
| 3 | Erbb2ip-5'geno-inside-F-9-12 | GATGCTCTTCAATAT GACATAAC (SEQ ID NO. 32) | KI: 676 bp Wt: none | Detection of 3-end |
| | Erbb2ip-5'geno-inside-R-9-12 | TCTGAGAGGCCCAAT GCCCAACG (SEQ ID NO. 33) | | |

The PCR procedure is as follows:

| Seg. | Temp. | Time | Cycle |
| --- | --- | --- | --- |
| 1 | 95° C. | 5 min | |
| 2 | 95° C. | 30 s | |
| 3 | 60° C. | 30 s | 2-4, 35x |
| 4 | 72° C. | 1 kb/min | |
| 5 | 72° C. | 5 min | |
| 6 | 10° C. | hold | |

The result of Cas9-mRNA+Erbb2ip donor targeting identification is as shown in FIG. 6. Among 90 test samples, 3 samples were identified as positive by PCR.

The result of Cas9-Protein+Erbb2ip donor targeting identification is as shown in FIG. 7. Among 85 test samples, 6 samples were identified as positive by PCR.

Example 5: a comparative test of the effects of the Cas9-mRNA and the Cas9 protein on the Ly101 gene targeting efficiency proves that the targeting efficiency of the Cas9-Protein+sgRNA+Donor combination is higher than that of the Cas9-mRNA+sgRNA+Donor combination.

Step 1: the sgRNA corresponding to a Ly101 gene was used, and the sequence of the sgRNA is as follows:

| sgRNA name | Sequence | PAM |
| --- | --- | --- |
| Ly101-5'sgRNA | GAGCTACCCTGAGTAGCAGA (SEQ ID NO. 34) | AGG |
| Ly101-3'sgRNA | CTGGTCATCAGCCAGCTAAG (SEQ ID NO. 35) | AGG |

A Ly101 gene targeting donor was used, and the sequence is as set forth in SEQ ID NO.36.

The sgRNA, donor, and Cas9 system were transferred into mouse fertilized eggs by microinjection or electroporation according to the method in the "Mouse Embryo Operation Experiment Manual", and the obtained embryos were tested for the gene targeting efficiency by nested PCR. The result shows that the Cas9-Protein+sgRNA+Donor combination has higher targeting efficiency than the Cas9-mRNA+sgRNA+Donor combination.

The specific targeting efficiency result is as follows:

| Name | Cleavage efficiency |
| --- | --- |
| Cas9-mRNA + Ly101 donor | 3.22% (3/93) |
| Cas9-Protein + Ly101 donor | 6.70% (11/164) |

The PCR system is as follows:

| Reagent | Volume (μl) | Specification |
| --- | --- | --- |
| 10x Buffer | 2.5 | \ |
| ddH$_2$O | 17.75 | \ |
| PrimerF | 0.5 | 10 μM |
| PrimerR | 0.5 | 10 μM |
| Mg2+ | 2 | 25 mM |
| dNTPs | 0.5 | 10 mM each |
| Taq | 0.25 | 5 U/μl |
| Template | 1 | ≈100 ng/μl |

PCR primers are as follows:

| No. | Primer name | Primer sequence | Stripe size | Primer description |
| --- | --- | --- | --- | --- |
| 1 | Ly101-5-geno-outside-F | ACCCCTAGCCTGGGCCTAGTTC (SEQ ID NO. 37) | Wt/wt = none KI/KI = 1220 bp | 5-end first round |
| | Ly101-5-geno-outside-R | TCGGAATTGAATATTTCTAGACCAGC (SEQ ID NO. 38) | | |
| 2 | Ly101-5-geno-inside-F | TTCTTCTGGCCCATAGAGACCA (SEQ ID NO. 39) | Wt/wt = none KI/KI = 1150 bp | 5-end second round |
| | Ly101-5-geno-inside-R | AGCTGGTTCTTTCCGCCTCAGA (SEQ ID NO. 40) | | |

-continued

| Primer No. | Primer name | Primer sequence | Stripe size | Primer description |
|---|---|---|---|---|
| 3 | Ly101-geno-outside-F2 | CTGGTGCTGCTAGTCTGGGTC CT (SEQ ID NO. 41) | Wt/wt = none | 3-end first round |
|   | Ly101-geno-outside-R2 | CAGCTTGTGGTAAACCTGAAG TGA (SEQ ID NO. 42) | KI/KI = 1544 bp |   |
| 4 | Ly101-geno-inside-F2 | CACCTAATTGCATCGCATTG (SEQ ID NO. 43) | Wt/wt = none | 3-end second round |
|   | Ly101-geno-inside-R2 | TGGCTGAACTGTAGCCTGCA (SEQ ID NO. 44) | KI/KI = 1292 bp |   |

The PCR procedure is as follows:

| Seg. | Temp. | Time | Cycle |
|---|---|---|---|
| 1 | 95° C. | 5 min |   |
| 2 | 95° C. | 30 s |   |
| 3 | 58° C. | 30 s | 2-4, 35x |
| 4 | 72° C. | 1 kb/min |   |
| 5 | 72° C. | 5 min |   |
| 6 | 10° C. | hold |   |

The result of Cas9-m+Ly101 donor targeting identification is as shown in FIG. 8. Among 93 test samples, 3 samples were identified as positive by PCR.

The result of Cas9-Protein+Ly101 donor targeting identification is as shown in FIG. 9. Among 164 test samples, 11 samples were identified as positive by PCR.

Example 6: a Gsdma123-Cas9-CKO mouse model was prepared, and F1 mice with the correct genotype identification can be used as animal models for studying the Gsdma gene.

Step 1: the sgRNA targeting a Gsdma locus was designed, and an sgRNA transcribe template was prepared.

The sgRNA targeting the Gsdma locus was designed using a Cas9sgRNA design website crispr.mit.edu, and a corresponding Oligo was ordered to construct the sgRNA.

The sgRNA sequences are as follows:

| sgRNA name | Sequence | PAM |
|---|---|---|
| Gsdma-5S1 | CTAGCAACAGGAGTATAAGT (SEQ ID NO. 45) | GGG |
| Gsdma-3S2 | CATCTTTCGATCCTTCTGCA (SEQ ID NO. 46) | TGG |

Forward and reverse primers were annealed to form double strands, and then the double strands were ligated with a pUC57-T7 universal vector singly digested with BsaI to construct a transcription vector containing the sgRNA sequence. The sequencing verification by a professional sequencing company showed that the target plasmid was obtained.

The obtained target plasmid was digested at 37° C. overnight. After completion, agarose gel electrophoresis was performed. The target strips were cut for gel recovery, and a final product obtained was recovered as a transcription template.

Step 2: all sgRNAs were transcribed in vitro using a transcription kit, and the transcribed sgRNAs were for later use.

Reagent I: HiScribe™ T7 Quick High Yield RNA Synthesis Kit (NEB #E2050S)

Reagent II: AmbionMEGAclear kit (AmbionAM1908)

In vitro transcription of the RNAs was carried out according to the operation manual of the HiScribe™ T7 Quick High Yield RNA Synthesis Kit (NEB #E2050S), and RNA purification was carried out according to the operation manual of the AmbionMEGAclear kit (AmbionAM1908).

Step 3: the sgRNA targeting Gsdma locus and the Cas9 protein were transferred into mouse fertilized eggs by microinjection or electroporation according to the method in the "Mouse Embryo Operation Experiment Manual". The obtained embryos were tested for sgRNA cleavage activity by nested PCR. The PCR products were sequenced and verified by a professional sequencing company, and a high-efficiency sgRNA was obtained by screening.

The PCR system is as follows:

| Reagent | Volume (μl) | Specification |
|---|---|---|
| 10x Buffer | 2.5 |   |
| ddH$_2$O | 17.75 |   |
| primerF | 0.5 | 10 μM |
| primerR | 0.5 | 10 μM |
| Mg2+ | 2 | 25 mM |
| dNTPs | 0.5 | 10 mM each |
| Taq | 0.25 | 5 U/μl |
| Template | 1 |   |

PCR primers are as follows:

| No. | Primer name | Primer sequence | Stripe size | Remarks |
|---|---|---|---|---|
| 1 | GSDMA-5out-F1 GSDMA-5out-R1 | ATGGCCCAATATCTATGTGT (SEQ ID NO. 47) AGTCCCTGTACTTGGACATC (SEQ ID NO. 48) | 1880 bp | First round PCR |
| 2 | GSDMA-5in-F1 GSDMA-5in-R1 | CCAAACTTGTGGTGCTTGCA (SEQ ID NO. 49) CCATGTTCACTTCTTCACAG (SEQ ID NO. 50) | 981 bp | Second round PCR |
| 3 | GSDMA-3out-F1 GSDMA-3out-R1 | GCCATCCTTTACTTCCTCGG (SEQ ID NO. 51) TTTGGGAGAAGTCATGGGCT (SEQ ID NO. 52) | 1800 bp | First round PCR |
| 4 | GSDMA-3in-F1 GSDMA-3in-R1 | AGGTATTTCAGAGGGAGAGA (SEQ ID NO. 53) TGTGTGTATATGTTGCGTGT (SEQ ID NO. 54) | 820 bp | Second round PCR |

The PCR procedure is as follows:

| Seg. | Temp. | Time | Cycle | ±Temp/cycle |
|---|---|---|---|---|
| 1 | 95° C. | 5 min |   |   |
| 2 | 95° C. | 30 s |   |   |
| 3 | 65° C. | 30 s |   | −0.5 |
| 4 | 72° C. | 1 min | 2-4, 20x |   |
| 5 | 95° C. | 30 s |   |   |
| 6 | 55° C. | 30 s |   |   |

-continued

| Seg. | Temp. | Time | Cycle | ±Temp/cycle |
|------|-------|------|-------|-------------|
| 7 | 72° C. | 1 min | 5-7, 20x | |
| 8 | 72° C. | 5 min | | |
| 9 | 10° C. | hold | | |

The sgRNA cleavage efficiency is as follows:

| sgRNA name | Cleavage efficiency (Range: 0-100%) | Predicted Efficiency (Range: 0-100) |
|------------|-------------------------------------|-------------------------------------|
| Gsdma-5S | 78 | 55 |
| Gsdma-3S | 53 | 57 |

Step 4: an Oligo targeting vector of Gsdma-Cas9-CKO and an identification scheme were designed and prepared. According to the targeting vector scheme, the targeting OligossDNA was ordered. The sequence is as follows:

```
Gadma123-Oligo-5:
                                      (SEQ ID NO. 55)
TGGAAAGGGGATATATCGTAAACAGAACTAACAAAGACAAAGAAGTAAGT

GAGAGAGAGGAACTGGGAAACAAGCCCGTGCACCCGCGGATAACTTCGTA

TAATGTATGCTATACGAAGTTATACTTATACTCCTGTTGCTAGGAGGTGG

GTGGGAAGGAAGTGTAGGGTACAAGCAAGTAGAGCCTTGCCAAGGAAAGG

Gadma123-Oligo-3:
                                      (SEQ ID NO. 56)
GGATTAAAGGCGTGCACCACCATGCCCAGCTTCCATTTTTATTTTTATTT

TTTGCTACATCTTTCGATCCTTCTGCAATAACTTCGTATAATGTATGCTA

TACGAAGTTATCCGCGGGGGCCCTGGTGCTAAGTCCATCACTTCCACATT

GCTGCCTGTCTGTTAGCTTTAATTCACAGTCACTACTCTTCTGATCTTGT
```

Step 5: embryo injection and transplantation

The synthetic OligossDNA, the Cas9 protein, the Gsdma-5 S, and the Gsdma-3 SsgRNA were mixed, and the mixed injection sample was provided to the injection personnel for carrying out embryo injection and transplantation.

Step 6: the mice born after transplantation were marked as F0, and sexually mature positive F0 with correct genotype identification was bred. The offspring mice were marked as F1, and the F1 mice were subjected to genotype identification. Positive F1 mice can be used as animal models for studying the Gsdma gene.

The identification result found that the PCR positive rate of the F0 mice obtained by the Gsdma-Oligo single-stranded vector and the Cas9 technology was 8.20% (5/61).

Genotype identification of F0 mice:
The PCR system of F0 is as follows:

| Reagent | Volume (μl) | Specification |
|---------|-------------|---------------|
| 10x Buffer | 2.5 | \ |
| ddH$_2$O | 16.75 | \ |
| PrimerF | 1 | 10 μM |
| PrimerR | 1 | 10 μM |
| Mg2+ | 2 | 25 mM |
| dNTPs | 0.5 | 10 mM each |
| Taq | 0.25 | 5 U/μl |
| Template | 1 | ≈100 ng/μl |

The PCR primers of F0 are as follows:

| Primer No. | Primer name | Primer sequence | Stripe size | Primer description |
|---|---|---|---|---|
| 1 | 21030ligo-5-loxp-TF | TCCAGCCCTTGACTTGAATC (SEQ ID NO. 57) | 275 bp | Positive: Identification of 5-end Loxp |
|  | 21030ligo-5-loxp-TR | TCAGAACTGGGCAGATTCCC (SEQ ID NO. 58) | 229 bp | Wt: |
| 2 | 21030ligo-3-loxp-TF | CAATCCAGGTATTTCAGAGG (SEQ ID NO. 59) | 440 bp | Positive: Identification of 3-end Loxp |
|  | 21030ligo-3-loxp-TR | GTGGGAAAATGTGTCGTGCA (SEQ ID NO. 60) | 394 bp | Wt: |

The PCR procedure of F0 is as follows:

| Seg. | Temp. | Time | Cycle | ±Temp/cycle |
|------|-------|------|-------|-------------|
| 1 | 95° C. | 5 min | | |
| 2 | 95° C. | 30 s | | |
| 3 | 65° C. | 30 s | 2-4, 20x | −0.5 |
| 4 | 72° C. | 30 s | | |
| 5 | 95° C. | 30 s | | |
| 6 | 55° C. | 30 s | | |
| 7 | 72° C. | 30 s | 5-7, 20x | |
| 8 | 72° C. | 5 min | | |
| 9 | 10° C. | hold | | |

The electrophoresis result of F0 genotype identification is as shown in FIG. 10. Among 61 mice, 5 mice were identified as positive by PCR.

Genotype identification of F1 mice:
The PCR system of F1 is as follows:

| Reagent | Volume (μl) | Specification |
|---------|-------------|---------------|
| 10x Buffer | 2.5 | \ |
| ddH$_2$O | 16.75 | \ |
| PrimerF | 1 | 10 μM |
| PrimerR | 1 | 10 μM |
| Mg2+ | 2 | 25 mM |
| dNTPs | 0.5 | 10 mM each |
| Taq | 0.25 | 5 U/μl |
| Template | 1 | ≈100 ng/μl |

The PCR primers of F1 are as follows:

| Primer No. | Primer name | Primer sequence | Stripe size | Primer description |
|---|---|---|---|---|
| 1 | 21030ligo-5-loxp-TF | TCCAGCCCTTGACTTGAATC (SEQ ID NO. 61) | 275 bp | Positive: Identification of 5-end Loxp |
|  | 21030ligo-5-loxp-TR | TCAGAACTGGGCAGATTCCC (SEQ ID NO. 62) | 229 bp | Wt: |
| 2 | 21030ligo-3-loxp-TF | CAATCCAGGTATTTCAGAGG (SEQ ID NO. 63) | 440 bp | Positive: Identification of 3-end Loxp |
|  | 21030ligo-3-loxp-TR | GTGGGAAAATGTGTCGTGCA (SEQ ID NO. 64) | 394 bp | Wt: |

The PCR procedure of F1 is as follows:

| Seg. | Temp. | Time | Cycle | ±Temp/cycle |
|---|---|---|---|---|
| 1 | 95° C. | 5 min | | |
| 2 | 95° C. | 30 s | | |
| 3 | 65° C. | 30 s | | −0.5 |
| 4 | 72° C. | 30 s | 2-4, 20x | |
| 5 | 95° C. | 30 s | | |
| 6 | 55° C. | 30 s | | |
| 7 | 72° C. | 30 s | 5-7, 20x | |
| 8 | 72° C. | 5 min | | |
| 9 | 10° C. | hold | | |

The electrophoresis result of genotype identification of F1 mice is as shown in FIG. 11.

The genotype identification result shows that 140 #, 141 #, 144 #, 145 #, 150-152 #, and 155 # were positive F1 mice with Loxp at both ends targeted.

What is claimed is:

1. A method for preparing Nestin-Cre (Nes-Cre) model mice by using Cas9 technology, comprising the following steps:
- step 1: preparation of a Cas9 protein with nuclease activity for subsequent steps, wherein the Cas9 protein is prepared by expression and purification in vitro;
- step 2: screening of sgRNA, comprising:
  - (1) designing a plurality of sgRNAs for targeting a Nes-Cre transgene to a knock-in locus and preparing transcription templates thereof, one of the plurality of sgRNAs being Nes-Cre-S2 consisting of a sequence as shown in SEQ ID NO: 4;
  - (2) transcribing the sgRNA in vitro using a transcription kit, and the transcribed sgRNA being for later use; and
  - (3) transferring the sgRNA from step 2(2) and the Cas9 protein from step 1 into mouse fertilized eggs by microinjection or electroporation, and testing the obtained embryos for sgRNA cleavage activity, thereby obtaining Nes-Cre-S2;
- step 3: construction of a single-stranded DNA targeting vector consisting of a sequence as shown in SEQ ID NO: 11, containing the Nes-Cre transgene;
- step 4: mouse embryo injection and transplantation, comprising:
  mixing the single-stranded DNA targeting vector constructed according to step 3, the Cas9 protein from step 1, and Nes-Cre-S2 from step 2, and carrying out mouse embryo injection and transplantation by using the mixed sample; and
- step 5: marking mice born after transplantation as F0 and carrying out the genotype identification of F0; breeding sexually mature F0 with the positive genotype identification, and marking the offspring mice thereof as F1; and analyzing and verifying the F1 mice, and the F1 mice with the positive genotype verification being the prepared Nes-Cre model mice.

* * * * *